US012778517B2

(12) United States Patent
Jia et al.

(10) Patent No.: US 12,778,517 B2
(45) Date of Patent: Nov. 3, 2026

(54) DIABETES RISK DETECTION METHOD, ELECTRONIC DEVICE, AND SYSTEM

(71) Applicants: HUAWEI TECHNOLOGIES CO., LTD., Shenzhen (CN); Peking Union Medical College Hospital, Chinese Academy of Medical Sciences, Beijing (CN)

(72) Inventors: Ziqian Jia, Beijing (CN); Luping Li, Beijing (CN); Maolin Chen, Shenzhen (CN)

(73) Assignees: Huawei Technologies Co., Ltd., Shenzhen (CN); Peking Union Medical College Hospital, Chinese Academy of Medical Sciences, Beijing (CN)

( * ) Notice: Subject to any disclaimer, the term of this patent is extended or adjusted under 35 U.S.C. 154(b) by 16 days.

(21) Appl. No.: 19/025,929

(22) Filed: Jan. 16, 2025

(65) Prior Publication Data

US 2025/0152107 A1 May 15, 2025

Related U.S. Application Data

(63) Continuation of application No. PCT/CN2023/107318, filed on Jul. 13, 2023.

(30) Foreign Application Priority Data

Jul. 30, 2022 (CN) ......................... 202210911487.3

(51) Int. Cl.
*A61B 5/00* (2006.01)
*A61B 5/024* (2006.01)
(Continued)

(52) U.S. Cl.
CPC ........ *A61B 5/7275* (2013.01); *A61B 5/02416* (2013.01); *A61B 5/681* (2013.01);
(Continued)

(58) Field of Classification Search
CPC ........ A61B 2562/0219; A61B 5/02416; A61B 5/1118; A61B 5/165; A61B 5/4806;
(Continued)

(56) References Cited

U.S. PATENT DOCUMENTS

2013/0024123 A1 1/2013 Ochs et al.
2017/0143279 A1 5/2017 Jayaraman et al.
(Continued)

FOREIGN PATENT DOCUMENTS

CN 105160199 A 12/2015
CN 111317484 A 6/2020
CN 109171694 B 4/2021

OTHER PUBLICATIONS

Usman et al., "Second Derivative and Contour Analysis of PPG for Diabetic Patients," 2018 IEEE-EMBS Conference on Biomedical Engineering and Sciences (IECBES), Total 4 pages (Dec. 2018).
(Continued)

*Primary Examiner* — Mark D Remaly
(74) *Attorney, Agent, or Firm* — Leydig, Voit & Mayer, Ltd.

(57) ABSTRACT

A diabetes risk detection method, an electronic device, and a system are disclosed and are applied to the field of terminal technologies, to resolve a problem in the conventional technology that an obtained diabetes risk detection result is inaccurate when time for collecting a photoplethysmography signal is short. The method includes: obtaining first data and second data, where the first data includes a photoplethysmography (PPG) signal obtained via a PPG sensor, and the second data includes one or more of the following: diet data, exercise data, physical symptom data, drug use data, sleep data, or emotion data; determining a diabetes risk
(Continued)

detection result based on the first data and the second data; and outputting the diabetes risk detection result to prompt a user with a health status.

20 Claims, 14 Drawing Sheets

(51) Int. Cl.
*G16H 10/60* (2018.01)
*G16H 50/30* (2018.01)

(52) U.S. Cl.
CPC .......... *A61B 5/7221* (2013.01); *G16H 10/60* (2018.01); *G16H 50/30* (2018.01)

(58) Field of Classification Search
CPC ..... A61B 5/681; A61B 5/6898; A61B 5/7221; A61B 5/7267; A61B 5/7275; G16H 10/60; G16H 20/10; G16H 20/30; G16H 20/60; G16H 20/70; G16H 40/63; G16H 40/67; G16H 50/30
See application file for complete search history.

(56) References Cited

U.S. PATENT DOCUMENTS

| | | | | |
|---|---|---|---|---|
| 2017/0215793 | A1 | 8/2017 | Newberry | |
| 2020/0258637 | A1 | 8/2020 | Jain et al. | |
| 2021/0401330 | A1* | 12/2021 | Frank ................ | A61B 5/14532 |

OTHER PUBLICATIONS

Philip et al., "Continous monitoring of blood glucose using photophlythesmograph signal," Proceedings of the IEEE International Conference on Innovations in Electrical, Electronics, Instrumentation and Media Technology (ICEEIMT), Total 5 pages (Feb. 2017).
Rashtian et al., "Heart Rate and CGM Feature Representation Diabetes Detection From Heart Rate: Learning Joint Features of Heart Rate and Continuous Glucose Monitors Yields Better Representations," IEEE Access, vol. 9, total 7 pages (Jun. 2021).
Srinivasan et al., "Deep Learning based non-invasive diabetes predictor using Photoplethysmography signals," 29th European Signal Processing Conference (EUSIPCO), Total 5 pages (Aug. 2021).
Tsai et al., "Diabetes Care in Motion: Blood Glucose Estimation Using Wearable Devices," IEEE Consumer Electronics Magazine, vol. 9, No. 1, Total 5 pages (Dec. 2019).

* cited by examiner

DIABETES RISK DETECTION METHOD, ELECTRONIC DEVICE, AND SYSTEM

CROSS-REFERENCE TO RELATED APPLICATIONS

This application is a continuation of International Patent Application No. PCT/CN2023/107318, filed on Jul. 13, 2023, which claims priority to Chinese Patent Application No. 202210911487.3, filed on Jul. 30, 2022. The disclosures of the aforementioned applications are hereby incorporated by reference in their entireties.

TECHNICAL FIELD

Embodiments of this application relate to the field of terminal technologies, and in particular, to a diabetes risk detection method, an electronic device, and a system.

BACKGROUND

Prevalence of diabetes is rising rapidly, and harm of the diabetes and complications of the diabetes is becoming more serious, resulting in rapid growth of medical expenses. Therefore, diabetes risk detection is of great significance. Conventional diabetes risk detection mainly relies on invasive and minimally invasive devices to collect blood and tissue fluid samples for blood glucose concentration analysis. Such an invasive or minimally invasive detection manner brings pain to a user, and requires a professional device, resulting in inconvenience. With advancement of science and technology, a wearable device may be used to collect physiological data of the user, to implement non-invasive diabetes risk detection. In a method for performing non-invasive diabetes risk detection via a wearable device provided in the conventional technology, when time for collecting physiological data (for example, a photoplethysmography (PPG) signal) is short, an obtained detection result is inaccurate.

SUMMARY

To resolve the foregoing technical problems, embodiments of this application provide a diabetes risk detection method, an electronic device, and a system. Technical solutions provided in embodiments of this application can be used to improve accuracy of a detection result when time for collecting a PPG signal is short.

To achieve the foregoing technical objective, embodiments of this application provide the following technical solutions.

According to a first aspect, a diabetes risk detection method is provided. The method includes: obtaining first data and second data, and determining a diabetes risk detection result based on the first data and the second data. Then, the diabetes risk detection result is output.

The first data includes various data that can reflect a diabetes feature and that is further used for diabetes risk detection. For example, the first data is a PPG signal obtained via a PPG sensor. The second data includes one or more of the following: diet data, exercise data, physical symptom data, drug use data, sleep data, and emotion data.

For example, the diet data includes one or more of the following: eating time, food taste or composition, and a degree of satiety. The exercise data includes one or more of the following: exercise time, duration, an exercise intensity, and an exercise frequency. The sleep data includes one or more of the following: a sleep time period, sleep duration, deep sleep or not, a deep sleep time period, and deep sleep duration. The drug use data includes one or more of the following: whether a drug is used, a drug type, and a drug use frequency. The emotion data includes one or more of the following: a psychological stress index and an emotion index.

For example, the first data may be obtained in the following manner: An electronic device obtains the first data via a built-in sensor; or an electronic device obtains the first data via another electronic device.

For example, the second data may be obtained in the following manner: The electronic device interacts with a user to obtain the second data. For example, one or more interfaces are displayed, where the one or more interfaces display the second data that needs to be provided by the user, and the second data entered by the user in the one or more interfaces is received; and/or the second data is obtained by an electronic device from another electronic device; and/or the second data is obtained from an installed application and/or service.

It can be learned that, in this embodiment of this application, the second data is collected, and comprehensive analysis is performed based on the second data and the first data. This is equivalent to that the diabetes risk detection result obtained based on the first data is calibrated by using the second data, to obtain a calibrated diabetes risk detection result. This improves accuracy of the detection result.

In a possible implementation, the obtaining first data and second data may be implemented as: detecting a trigger operation of diabetes risk detection of the user; and obtaining the first data and the second data in response to the trigger operation.

In other words, in this implementation, diabetes risk detection is performed after being triggered by the user.

In a possible implementation, the determining a diabetes risk detection result based on the first data and the second data may be implemented as: determining a first risk value based on the first data. A second risk value is obtained based on the second data and the first risk value. The second risk value may indicate the diabetes risk detection result.

Optionally, the first risk value is adjusted based on the second data, to obtain the second risk value.

In a possible implementation, an implementation of obtaining the second risk value based on the second data and the first risk value is provided, in other words, obtaining the second risk value based on the second data and the first risk value may be implemented as: obtaining the second risk value based on weights corresponding to different second data and the first risk value.

Optionally, the first risk value is adjusted based on the weights corresponding to different second data, to obtain the second risk value. A weight of one type or one piece of second data indicates a degree of impact of the second data on the detection result. A greater degree of impact of one type or one piece of second data on the detection result indicates a larger corresponding weight, and correspondingly, the second data has a larger adjustment amplitude for the first risk value. The weights may be preset. In other words, the first risk value is increased or decreased based on degrees of impact of different second data on diabetes. If one type or one piece of second data has large impact on diabetes, a corresponding adjustment amplitude is large. Correspondingly, if one type or one piece of second data has small impact on diabetes, a corresponding adjustment amplitude is small.

In a possible implementation, the method further includes: outputting confidence of the diabetes risk detection result. The confidence indicates accuracy of the diabetes risk detection result.

Optionally, the confidence is determined based on at least one or more of the following: duration of the obtained first data, whether the obtained first data is missing within a preset time period, quality of the obtained first data, a type of the obtained second data, a level of detail of the obtained second data, and the like.

Longer duration and higher quality of the collected first data, more types of the collected second data, and more detailed second data indicate higher confidence of the detection result.

In a possible implementation, after the confidence is obtained, because the confidence is related to the second data, the user may be further prompted with an association relationship between the confidence and the second data, that is, the confidence is obtained from which second data. Therefore, the method further includes: prompting the user with the confidence of the diabetes risk detection result and the second data corresponding to the confidence.

In a possible implementation, when the confidence is less than a preset threshold, the user is prompted to edit the obtained second data or enter more second data (which may also be described as third data in this application).

In this way, the user is continuously guided to enter more second data, so that the confidence of the diabetes risk detection result can be improved.

In a possible implementation, the obtaining second data includes: obtaining second data within a preset time period. The preset time period includes one or more of the following time periods: a time period in which first data is missing, a nap time period, a diet time period, and a night sleep time period.

In this way, for some specific time periods, only the second data in the specific time periods is collected, so that a data volume of the obtained second data can be reduced, and an interaction load of the user and a processing load of the electronic device can be reduced.

In a possible implementation, the second data includes a plurality of types of second data. The obtaining first data and second data, and determining a diabetes risk detection result based on the first data and the second data includes:

obtaining the first data; obtaining the second data in descending order of priorities of different second data; and stopping obtaining the second data if it is determined, based on the obtained second data and the first data, that the confidence of the obtained diabetes risk detection result is greater than or equal to the preset threshold.

If it is determined, based on the obtained second data and the obtained first data, that the confidence of the obtained diabetes risk detection result is less than the preset threshold, the second data continues to be obtained until the confidence of the diabetes risk detection result is greater than or equal to the preset threshold.

Priorities of different pieces or types of second data corresponding to different users are different or the same.

Compared with a case in which the user needs to fill in all the second data at a time, this manner can reduce a data volume of the second data filled in by the user, and reduce an interaction load of the user. For example, it is assumed that the physical symptom data, the drug use data, the diet data, and the exercise data are separately located on different pages. In comparison with a case in which the user turns pages between the three pages and fills in all data on the three pages, in this manner of filling based on the priorities, the user may need to fill in only one type of content (that is, content on one page) of the physical symptom data and the drug use data, and does not need to fill in other second data. This reduces the interaction load of the user.

According to a second aspect, an electronic device is provided. The electronic device includes a processor and a memory. The memory is coupled to the processor. The memory is configured to store computer-readable instructions. When the processor reads the computer-readable instructions from the memory, the electronic device is enabled to perform the following operations: obtaining first data and second data, and determining a diabetes risk detection result based on the first data and the second data. Then, the diabetes risk detection result is output.

In a possible implementation, the obtaining first data and second data may be implemented as: detecting a trigger operation of diabetes risk detection of a user; and obtaining the first data and the second data in response to the trigger operation.

In a possible implementation, the determining a diabetes risk detection result based on the first data and the second data may be implemented as: determining a first risk value based on the first data. A second risk value is obtained by adjusting the first risk value based on the second data. The second risk value may indicate the diabetes risk detection result.

In a possible implementation, the adjusting the first risk value based on the second data to obtain a second risk value may be implemented as: adjusting the first risk value based on the weights of different second data to obtain the second risk value.

In a possible implementation, when the processor reads the computer instructions from the memory, the electronic device is further enabled to perform the following operation: outputting confidence of the diabetes risk detection result. The confidence indicates accuracy of the diabetes risk detection result.

In a possible implementation, the confidence is determined based on at least one or more of the following: duration of the obtained first data, whether the obtained first data is missing within a preset time period, quality of the obtained first data, a type of the obtained second data, and a level of detail of the obtained second data.

In a possible implementation, when the processor reads the computer instructions from the memory, the electronic device is further enabled to perform the following operation: prompting the user with the confidence of the diabetes risk detection result and the second data corresponding to the confidence.

In a possible implementation, when the processor reads the computer instructions from the memory, the electronic device is further enabled to perform the following operation: when the confidence is less than a preset threshold, prompting the user to edit the obtained second data or enter third data.

In a possible implementation, the obtaining second data includes: obtaining second data within a preset time period. The preset time period includes one or more of the following time periods: a time period in which first data is missing, a nap time period, a diet time period, and a night sleep time period.

In a possible implementation, the second data includes a plurality of types of second data. The obtaining first data and second data, and determining a diabetes risk detection result based on the first data and the second data includes:

obtaining the first data; obtaining second data with a high priority based on priorities of different second data; and stopping obtaining the second data if it is determined, based on the second data with the high priority and the first data, that the confidence of the diabetes risk detection result is greater than or equal to the preset threshold.

Otherwise, if it is determined, based on the second data with the high priority and the first data, that the confidence of the obtained diabetes risk detection result is less than the preset threshold, second data with a low priority is obtained, and the diabetes detection result is determined based on the obtained second data and the obtained first data until the confidence of the diabetes risk detection result is greater than or equal to the preset threshold.

For technical effect corresponding to the second aspect and any one of the implementations of the second aspect, refer to technical effect corresponding to the first aspect and any one of the implementations of the first aspect. Details are not described herein again.

According to a third aspect, an embodiment of this application provides an electronic device. The electronic device has a function of implementing the diabetes risk detection method according to the first aspect and any one of the implementations of the first aspect. The function may be implemented by hardware, or may be implemented by hardware executing corresponding software. The hardware or the software includes one or more modules corresponding to the function.

For technical effect corresponding to the third aspect and any one of the implementations of the third aspect, refer to technical effect corresponding to the first aspect and any one of the implementations of the first aspect. Details are not described herein again.

According to a fourth aspect, a computer-readable storage medium is provided. The computer-readable storage medium stores a computer program (which may also be referred to as instructions or code). When the computer program is executed by an electronic device, the electronic device is enabled to perform the method in the first aspect or any one of the implementations of the first aspect.

For technical effect corresponding to the fourth aspect and any one of the implementations of the fourth aspect, refer to technical effect corresponding to the first aspect and any one of the implementations of the first aspect. Details are not described herein again.

According to a fifth aspect, an embodiment of this application provides a computer program product. When the computer program product runs on an electronic device, the electronic device is enabled to perform the method according to the first aspect or any one of the implementations of the first aspect.

For technical effect corresponding to the fifth aspect and any one of the implementations of the fifth aspect, refer to technical effect corresponding to the first aspect and any one of the implementations of the first aspect. Details are not described herein again.

According to a sixth aspect, an embodiment of this application provides a circuit system. The circuit system includes a processing circuit, and the processing circuit is configured to perform the method according to the first aspect or any one of the implementations of the first aspect.

For technical effect corresponding to the sixth aspect and any one of the implementations of the sixth aspect, refer to technical effect corresponding to the first aspect and any one of the implementations of the first aspect. Details are not described herein again.

According to a seventh aspect, an embodiment of this application provides a chip system, including at least one processor and at least one interface circuit. The at least one interface circuit is configured to perform a transceiver function, and send instructions to the at least one processor. When the at least one processor executes the instructions, the at least one processor performs the method according to the first aspect or any one of the implementations of the first aspect.

For technical effect corresponding to the seventh aspect and any one of the implementations of the seventh aspect, refer to technical effect corresponding to the first aspect and any one of the implementations of the first aspect. Details are not described herein again.

According to an eighth aspect, an embodiment of this application provides a diabetes risk detection system. The system includes a first electronic device and a second electronic device. The first electronic device is configured to perform the method according to the first aspect or any one of the implementations of the first aspect, and the second electronic device is configured to obtain first data and/or second data, and then send the first data and/or the second data to the first electronic device.

For technical effect corresponding to the eighth aspect and any one of the implementations of the eighth aspect, refer to technical effect corresponding to the first aspect and any one of the implementations of the first aspect. Details are not described herein again.

BRIEF DESCRIPTION OF DRAWINGS

FIG. 4A-1 and FIG. 4A-2 are a diagram 1 of interfaces according to an embodiment of this application;

FIG. 4B-1 to FIG. 4B-3 are a diagram 2 of interfaces according to an embodiment of this application;

DESCRIPTION OF EMBODIMENTS

Figure 1:
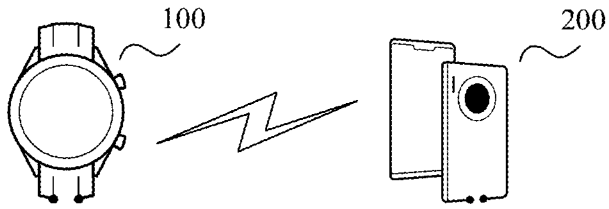
FIG. 1 is a diagram of a structure of a system according to an embodiment of this application.

The following describes technical solutions in embodiments of this application with reference to accompanying drawings in embodiments of this application. In the descriptions of embodiments of this application, terms used in the following embodiments are merely intended for a purpose of describing specific embodiments, but are not intended to limit this application. Terms "one", "a", "the", "the foregoing", "this", and "the one" of singular forms used in this specification and the appended claims of this application are also intended to include expressions such as "one or more", unless otherwise specified in the context clearly. It should be further understood that, in the following embodiments of this application, "at least one" and "one or more" mean one or more (including two).

Reference to "an embodiment", "some embodiments", or the like described in this specification indicates that one or more embodiments of this application include a specific feature, structure, or characteristic described with reference to embodiments. Therefore, statements such as "in an embodiment", "in some embodiments", "in some other embodiments", and "in other embodiments" that appear at different places in this specification do not necessarily mean referring to a same embodiment. Instead, the statements mean "one or more but not all of embodiments", unless otherwise specifically emphasized in another manner. Terms "include", "contain", "have", and their variants all mean "include but are not limited to", unless otherwise specifically emphasized in another manner. The term "connection" includes a direct connection and an indirect connection, unless otherwise stated. "First" and "second" are merely intended for a purpose of description, and shall not be understood as an indication or implication of relative importance or implicit indication of a quantity of indicated technical features.

In embodiments of this application, words such as "example" or "for example" are used to represent giving examples, illustrations, or descriptions. Any embodiment or design scheme described as an "example" or "for example" in embodiments of this application should not be construed as being more preferred or more advantageous than another embodiment or design scheme. Exactly, use of the term "example", "for example", or the like is intended to present a related concept in a specific manner.

With advancement of science and technology, a wearable device may be used to implement non-invasive diabetes risk detection. For example, a study finds that there are many common points in physiological mechanisms of blood glucose regulation and heart beat. Therefore, a blood volume change process may be detected through photoplethysmography (PPG), to reflect blood glucose regulation and cardiovascular health information. Based on this principle, a PPG sensor is built in a wearable device (for example, a wearable watch or a wearable band). A PPG signal is collected via the sensor, and a feature related to diabetes is extracted based on the PPG signal, to detect a risk of diabetes of a user.

In a related solution, a user wears a wearable device with a built-in PPG sensor. The wearable device captures a pulse signal via the PPG sensor, and preprocesses the pulse signal to obtain a waveform corresponding to the pulse signal. A plurality of peaks in the waveform are detected, and a first group of characteristic parameters are extracted from the plurality of peaks. A user without diabetes, a user in pre-diabetes, and a user with diabetes are separately used as control groups, and a second group of characteristic parameters are separately extracted from a waveform of a pulse signal corresponding to each control group. The first group of characteristic parameters is compared with the second group of characteristic parameters. Finally, it is determined, based on a comparison result, whether the user is in a normal state, a pre-diabetic state, or a diabetic state.

In another related solution, the user wears the wearable device with the built-in PPG sensor. The wearable device obtains the pulse signal via the PPG sensor, and performs frequency domain analysis, linear analysis, non-linear analysis, and the like on the pulse signal to obtain information like a pulse rate (PR) sequence in the pulse signal. Further, a required pulse signal feature indicator is obtained through analysis. A diabetes condition evaluation result is obtained based on the pulse signal feature indicator obtained through analysis and a model function of a pre-established correspondence between the pulse signal feature indicator and a diabetes condition.

In the foregoing related solution, diabetes risk detection is performed based on the pulse signal. When quality of the pulse signal is poor and collection time is short, accuracy of an obtained diabetes risk detection result is low.

To improve accuracy of the detection result, the pulse signal usually needs to be collected for a long time, and then a diabetes risk level of the user in this time period is evaluated when collected pulse signal data is sufficient. However, in this solution of collecting the pulse signal for a long time, a period of collecting the pulse signal is long, and the user needs to wait for a long time before a risk assessment result is provided. This easily causes anxiety of the user and the like. In addition, the detection result obtained through this solution reflects an average diabetes risk level of the user in this period of time. In actual life, the user may be further concerned about a diabetes risk level in a short time (for example, a previous day or recent days), and the solution of collecting the pulse signal for a long time cannot meet the requirement of the user. Therefore, although accuracy of the diabetes risk detection result can be improved through the solution in which the pulse signal is collected for a long time, user experience brought by this solution is poor.

To resolve a problem existing in an existing related solution, an embodiment of this application provides a non-invasive diabetes risk detection method, to improve accuracy of a diabetes risk detection result obtained after physiological data (for example, a PPG signal) of a user is collected in a short time.

The diabetes risk detection method provided in this embodiment of this application may be applied to a system including a plurality of electronic devices. The plurality of electronic devices include a wearable device and another electronic device, a plurality of wearable devices, a plurality of other electronic devices, and the like. A quantity of the electronic devices included in the system is not limited in embodiments of this application.

For example, as shown in FIG. 1, the system is a system including a wearable device 100 and another electronic device 200.

For example, the wearable device 100 may be a terminal device, for example, a smart watch, a smart band, a smart ankle, a wireless headset, smart glasses, or a smart helmet. An operating system installed on the wearable device includes but is not limited to iOS®, Android®, Harmony®, Windows®, Linux®, or another operating system. In some embodiments, the wearable device may be a fixed device, or may be a portable device. A specific type of the wearable device and the installed operating system are not limited in this application.

For example, the another electronic device 200 may be a terminal device, for example, a mobile phone, a personal computer (PC), a tablet computer (tablet), a notebook computer, a desktop computer, a notebook computer, a computer with a transceiver function, a wearable device, a vehicle-mounted device, or an artificial intelligence (AI) device. An operating system installed on the another electronic device includes but is not limited to iOS®, Android®, Harmony®, Windows®, Linux®, or another operating system. In some embodiments, the another electronic device may be a fixed device, or may be a portable device. A specific type of the another electronic device and the installed operating system are not limited in this application either.

In FIG. 1, an example in which one wearable device and one another electronic device are included is used for description. In actual application, there may be a plurality of wearable devices and/or other electronic devices.

In the system, the wearable device 100 may establish a communication connection to the another electronic device 200 through a wired communication technology and/or a wireless communication technology. The wireless communication technology includes but is not limited to at least one of the following: near field communication (NFC), Bluetooth (BT) (for example, conventional Bluetooth or Bluetooth low energy (BLE)), a wireless local area network (WLAN) (for example, a wireless fidelity (Wi-Fi) network), ZigBee, frequency modulation (FM), infrared (IR), and the like.

In some embodiments, both the wearable device 100 and the another electronic device 200 support a proximity discovery function. For example, after the wearable device approaches the another electronic device, the wearable device and the another electronic device can discover each other, and then establish a wireless communication connection like a Wi-Fi peer-to-peer (P2P) connection or a Bluetooth connection. After the wireless communication connection is established, the wearable device may exchange a signal with the another electronic device through the wireless communication connection.

In some embodiments, the wearable device 100 establishes a wireless communication connection to the another electronic device 200 via a local area network. For example, the wearable device 100 and the another electronic device 200 are connected to a same router.

In some embodiments, the wearable device 100 establishes a wireless communication connection to the another electronic device 200 via a cellular network, the Internet, or the like. For example, the another electronic device 200 accesses the Internet via the router, and the wearable device 100 accesses the Internet via the cellular network. Further, the wearable device 100 establishes a wireless communication connection to the another electronic device 200.

In some embodiments, the wearable device 100 and the another electronic device 200 collaboratively obtain first data and second data that are used for diabetes risk detection, and further perform comprehensive analysis based on the first data and the second data, to obtain a diabetes risk detection result of a user. In embodiments of this application, a specific device that obtains specific data is not limited, and a device that comprehensively analyzes the obtained data is not limited.

For example, the wearable device 100 obtains the first data used for diabetes risk detection. The another electronic device 200 obtains the second data. The second data includes at least one of the following: basic information of the user, such as age, gender, height, and weight, exercise data, sleep data, emotion data, physical symptom data, and drug use data. For a specific explanation of the second data, refer to the following description. The wearable device 100 sends the obtained first data to the another electronic device 200, and the another electronic device 200 performs comprehensive analysis based on the first data and the second data, to obtain the diabetes risk detection result of the user.

For another example, the wearable device 100 obtains the first data used for diabetes risk detection, and the another electronic device 200 obtains the second data. For the second data, refer to the foregoing descriptions. The another electronic device 200 sends the obtained second data to the wearable device 100. The wearable device 100 performs comprehensive analysis based on the first data and the second data, to obtain the diabetes risk detection result of the user.

For another example, the wearable device 100 obtains the first data used for diabetes risk detection, and the another electronic device 200 obtains a part of the second data, for example, the basic information of the user, the physical symptom data, and the drug use data. The wearable device obtains a part of the second data, for example, the exercise data and the sleep data. Then, the wearable device sends the obtained first data and the obtained second data to the another electronic device 200, and the another electronic device 200 performs comprehensive analysis on the first data and the second data that are obtained from the wearable device and the second data obtained by the another electronic device 200, to obtain the diabetes risk detection result of the user.

For another example, the wearable device 100 obtains the first data used for diabetes risk detection, and the another electronic device 200 obtains a part of the second data, for example, the basic information of the user, the physical symptom data, and the drug use data. The wearable device obtains a part of the second data, for example, the exercise data and the sleep data. Then, the another electronic device 200 sends the obtained second data to the wearable device 100. The wearable device 100 performs comprehensive analysis on the first data and the second data that are obtained by the wearable device 100 and the second data obtained from the another electronic device 200, to obtain the diabetes risk detection result of the user.

Figure 2:
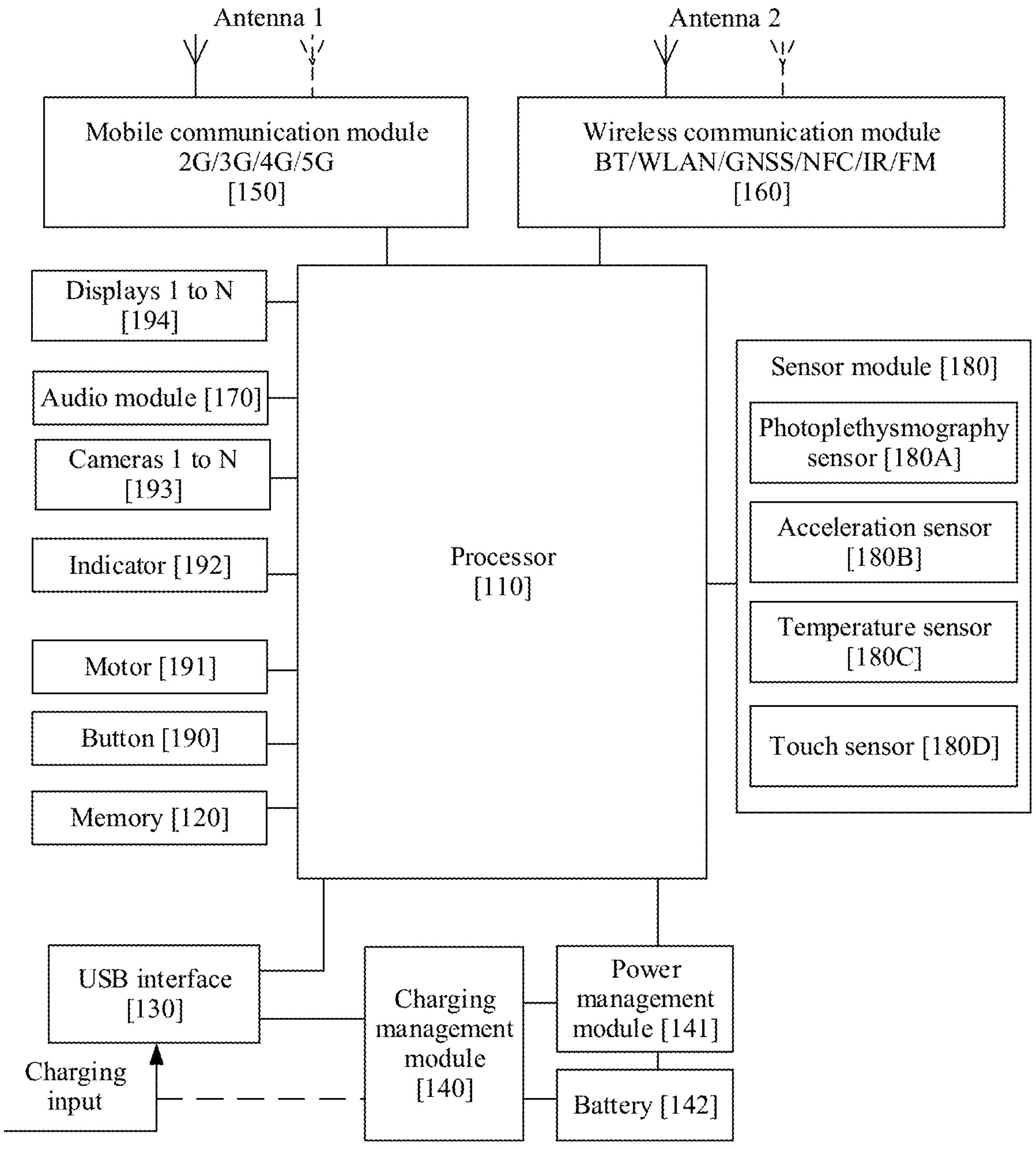
FIG. 2 is a diagram of a structure of a wearable device according to an embodiment of this application.

For example, FIG. 2 is a diagram of a structure of the wearable device 100.

The wearable device 100 may include a processor 110, a memory 120, a universal serial bus (USB) interface 130, a charging management module 140, a power management module 141, a battery 142, an antenna 1, an antenna 2, a mobile communication module 150, a wireless communication module 160, an audio module 170, a sensor module 180, a button 190, a motor 191, an indicator 192, a camera 193, a display 194, and the like. The sensor module 180 may include a photoplethysmography sensor 180A, an acceleration (ACC) sensor 180B, a temperature sensor 180C, a touch sensor 180D, and the like.

The processor 110 may include one or more processing units. For example, the processor 110 may include an application processor (AP), a modem processor, a graphics processing unit (GPU), an image signal processor (ISP), a controller, a video codec, a digital signal processor (DSP), a baseband processor, and/or a neural-network processing unit (NPU), and the like. Different processing units may be independent components, or may be integrated into one or more processors.

The controller may generate an operation control signal based on an instruction operation code and a time sequence signal, to complete control of instruction reading and instruction execution.

A memory may be further disposed in the processor 110, and is configured to store instructions and data. In some embodiments, the memory in the processor 110 is a cache memory. The memory may store instructions or data that has been used or cyclically used by the processor 110. If the processor 110 needs to use the instructions or the data again, the processor 110 may directly invoke the instructions or the data from the memory. This avoids repeated access, reduces waiting time of the processor 110, and improves system efficiency.

In some embodiments, the processor 110 may include one or more interfaces, for example, the USB interface 130. The USB interface 130 is an interface that conforms to a USB standard specification, and may be specifically a mini USB interface, a micro USB interface, a USB type-C interface, or the like. The USB interface 130 may be configured to connect to a charger to charge the wearable device 100, or may be configured to transmit data between the wearable device 100 and a peripheral device, or may be configured to connect to a headset for playing audio through the headset. The interface may be further configured to connect to another device, for example, an augmented reality (AR) device.

The charging management module 140 is configured to receive a charging input from a charger. The charger may be a wireless charger or a wired charger.

The power management module 141 is configured to connect to the battery 142, the charging management module 140, and the processor 110. The power management module 141 receives an input from the battery 142 and/or the charging management module 140, to supply power to the processor 110, the memory 120, the display 194, the camera 193, the wireless communication module 160, and the like.

A wireless communication function of the wearable device 100 may be implemented through the antenna 1, the antenna 2, the mobile communication module 150, the wireless communication module 160, and the like.

The antenna 1 and the antenna 2 are configured to transmit and receive an electromagnetic wave signal. Each antenna in the wearable device 100 may be configured to cover one or more communication frequency bands. Different antennas may be further multiplexed, to improve antenna utilization. For example, the antenna 1 may be multiplexed as a diversity antenna of a wireless local area network. In some other embodiments, the antenna may be used in combination with a tuning switch.

The mobile communication module 150 may provide a wireless communication solution that is applied to the wearable device 100 and that includes 2G, 3G, 4G, 5G, and the like. The mobile communication module 150 may include at least one filter, a switch, a power amplifier, a low noise amplifier (LNA), and the like.

The wireless communication module 160 may provide a wireless communication solution that is applied to the wearable device 100 and that includes a wireless local area network (WLAN) (for example, a wireless fidelity (Wi-Fi) network), Bluetooth (BT), a global navigation satellite system (GNSS), frequency modulation (FM), a near field communication (NFC) technology, an infrared (IR) technology, or the like.

In some embodiments, the antenna 1 and the mobile communication module 150 in the wearable device 100 are coupled, and the antenna 2 and the wireless communication module 160 are coupled, so that the wearable device 100 can communicate with a network and another device by using a wireless communication technology.

The wearable device 100 may implement a display function through the GPU, the display 194, the application processor, and the like. The GPU is a microprocessor for image processing, and is connected to the display 194 and the application processor. The GPU is configured to: perform mathematical and geometric computation, and render an image. The processor 110 may include one or more GPUs, which execute program instructions to generate or change display information.

The display 194 is configured to display an image, a video, and the like. The display 194 includes a display panel. The display panel may be made of a liquid crystal display (LCD), for example, an organic light emitting diode (OLED), an active-matrix organic light emitting diode (AMOLED), a flexible light emitting diode (FLED), a mini-LED, a micro-LED, a micro-OLED, or a quantum dot light emitting diode (QLED). In some embodiments, the wearable device 100 may include one or N displays 194, where N is a positive integer greater than 1.

The camera 193 is configured to capture a static image or a video. In some embodiments, the wearable device 100 may include one or N cameras 193, where N is a positive integer greater than 1.

The memory 120 may be configured to store computer-executable program code. The executable program code includes instructions. The memory 120 may include a program storage area and a data storage area. The program storage area may store an operating system, an application required by at least one function (for example, a voice playing function or an image playing function), and the like. The data storage area may store data (for example, the first data and the second data) created in a use process of the wearable device 100, and the like. In addition, the memory 120 may include a high-speed random access memory, and may further include a non-volatile memory, for example, at least one magnetic disk storage component, a flash memory component, or a universal flash storage (UFS). The processor 110 runs the instructions stored in memory 120 and/or instructions stored in a memory disposed in the processor, to perform various function applications of the wearable device 100 and data processing.

The wearable device 100 may implement an audio function, for example, music playing or recording via the audio module 170, the application processor, and the like.

The audio module 170 is configured to convert digital audio information into an analog audio signal for output, and is also configured to convert analog audio input into a digital audio signal. The audio module 170 may be further configured to code and decode an audio signal. In some embodiments, the audio module 170 may be disposed in the processor 110, or some functional modules in the audio module 170 are disposed in the processor 110. The wearable device 100 may perform, for example, music playing or recording, via the audio module 170. The audio module 170 may include a speaker, a receiver, a microphone, an application processor, and the like.

The photoplethysmography sensor 180A may obtain, through photoplethysmography (PPG) by measuring attenuation light reflected and absorbed by human blood vessels and tissue, a PPG signal based on a light emitting diode (LED) light source and a detector. A principle of photoplethysmography is as follows: When light passes through skin tissue and then is reflected to a photosensitive sensor, the light is attenuated to some extent. On the premise that the user does not perform large-scale exercise, absorption of light by muscles, bones, veins, other connecting tissue, and the like basically remains unchanged, but absorption of light by blood changes. Because the blood flows in arteries, absorption of light also changes naturally. When light is converted into an electrical signal, because absorption of light by the arteries changes and absorption of light by other tissues basically remain unchanged, obtained signals may be classified into a direct current (DC) signal and an alternating current (AC) signal. A characteristic of blood flow can be obtained by analyzing the extracted AC signal. The wearable device 100 collects the PPG signal via the photoplethysmography sensor 180A for analysis, to obtain physiological data of the user, for example, a heart rate, a respiratory rate, and blood oxygen. In some embodiments of this application, a diabetes-related feature is extracted by analyzing the PPG signal, to detect a diabetes risk of the user.

The acceleration sensor 180B may detect accelerations in various directions (usually on three axes) of the wearable device 100. When the wearable device 100 is static, a magnitude and a direction of gravity may be detected. The acceleration sensor 180B may be further configured to identify a posture of the wearable device, and is used in an application such as switching between a landscape mode and a portrait mode or a pedometer. In some embodiments of this application, the acceleration sensor 180B measures an acceleration signal. The acceleration signal may be used to determine a status of the user, for example, a static state or a moving state. The physiological data (for example, the respiratory rate, the heart rate, the blood oxygen, and blood glucose) of the user may vary in different states. Therefore, to improve accuracy of the obtained physiological data of the user, the wearable device 100 may further determine the status of the user by using the acceleration signal collected by the acceleration sensor 180B.

The temperature sensor 180C is configured to detect a temperature. In some embodiments, the wearable device 100 executes a temperature processing policy based on the temperature detected by the temperature sensor 180C. For example, when the temperature reported by the temperature sensor 180C exceeds a threshold, the wearable device 100 lowers performance of a processor nearby the temperature sensor 180C, to reduce power consumption for thermal protection. In some other embodiments, when the temperature is less than another threshold, the wearable device 100 heats the battery 142 to prevent the wearable device 100 from being shut down abnormally due to a low temperature. In some other embodiments, when the temperature is less than still another threshold, the wearable device 100 boosts an output voltage of the battery 142 to avoid abnormal shutdown due to a low temperature.

The touch sensor 180D is also referred to as a “touch device”. The touch sensor 180D may be disposed on the display 194, and the touch sensor 180D and the display 194 constitute a touchscreen, which is also referred to as a “touch screen”. The touch sensor 180D is configured to detect a touch operation performed on or near the touch sensor. The touch sensor may transfer a detected touch operation to the application processor to determine a touch event type. A visual output related to the touch operation may be provided through the display 194. In some other embodiments, the touch sensor 180D may be alternatively disposed on a surface of the wearable device 100, and is located at a location different from that of the display 194.

Optionally, the sensor module 180 may further include a pressure sensor, a barometric pressure sensor, a magnetic sensor, a distance sensor, an optical proximity sensor, a gyroscope sensor, a fingerprint sensor, an ambient optical sensor, a bone conduction sensor, and the like.

The button 190 includes a power button, a volume button, and the like. The button 190 may be a mechanical button, or may be a touch button. The wearable device 100 may receive an input of the button, and generate a button signal input related to a user setting and function control of the wearable device 100.

The motor 191 may generate a vibration prompt. The motor 191 may be configured to provide an incoming call vibration prompt and touch vibration feedback.

The indicator 192 may be an indicator light, and may be configured to indicate a charging status and a power change, or may be configured to indicate a message, a missed call, a notification, and the like.

Figure 3:
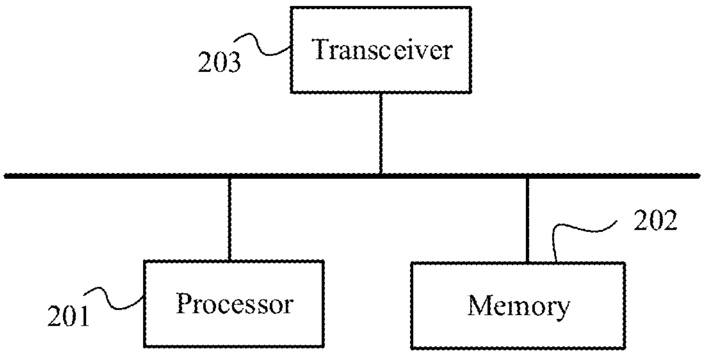
FIG. 3 is a diagram of a structure of another wearable device according to an embodiment of this application.

It may be understood that the foregoing is merely an example for describing a structure of the wearable device in this embodiment of this application, and does not constitute a limitation on the structure and a form of the wearable device. The structure and the form of the wearable device are not limited in this embodiment of this application. For example, FIG. 3 shows another example structure of the wearable device. As shown in FIG. 3, the wearable device includes a processor 201, a memory 202, and a transceiver 203. For implementations of the processor 201 and the memory 202, refer to the foregoing implementations of the processor and the memory. The transceiver 203 is configured to enable the wearable device to interact with another device (for example, a mobile phone). The transceiver 203 may be a device based on Wi-Fi, Bluetooth, or another communication protocol.

In some other embodiments of this application, the wearable device may include more or fewer components than those shown in FIG. 2 and FIG. 3, or some components may be combined, or some components may be split, or some components may be replaced, or different component arrangements may be used. The components shown in the figure may be implemented by hardware, software, or a combination of software and hardware.

Optionally, for a structure of the electronic device 200, refer to the structure of the wearable device 100. The electronic device 200 may have more or fewer structures than the wearable device 100. This is not specifically limited in this application.

The diabetes risk detection method provided in embodiments of this application is applied to any other electronic device that can obtain the first data and the second data that are used for diabetes risk detection, for example, any apparatus, like a mobile phone or a wearable device including the structure shown in FIG. 2 or FIG. 3.

Embodiments of this application provide a non-invasive diabetes risk detection method. In the method, first data and second data that are used for diabetes risk detection are obtained, for example, basic information (such as age, gender, height, and weight) of a user, diet data, exercise data, health data, and sleep data. A diabetes risk detection result can be obtained in a short time through comprehensive analysis based on the second data and the first data used for diabetes risk detection. The detection result is obtained by calibrating, by using the second data, a result obtained based on the first data used for diabetes risk detection, so that accuracy of a short-term detection result can be improved.

In embodiments of this application, the first data includes various data that can reflect a diabetes feature and that is further used for diabetes risk detection. Optionally, some wearable devices each may have a built-in PPG sensor, and obtain a PPG signal (the PPG signal may be obtained through analysis based on a pulse signal, a signal obtained by pressing a finger, or the like) via the PPG sensor, analyze the PPG signal, and extract a feature related to diabetes to detect a diabetes risk. Therefore, the first data may be the PPG signal. Optionally, some wearable devices each may be built in an eye, and monitor a blood glucose level of a wearer by analyzing a glucose content in tears of the wearer. Therefore, the first data may be a blood glucose value.

Optionally, some wearable devices each may be worn on a finger. Blood flow is temporarily blocked by giving pressure to the finger, to form new blood power, and unique optical signals are generated. The diabetes risk can be detected by analyzing these signals. Therefore, the first data may alternatively be the optical signal. In conclusion, a type of the first data is not limited in embodiments of this application.

In embodiments of this application, the second data is used to reflect life information of the user, and may cover all aspects of life of the user. Optionally, the second data includes at least one of the following data: the basic information, the diet data, the exercise data, physical symptom data, drug use data, the sleep data, and the like. The basic information of the user includes the age, the gender, the height, and the weight of the user. The diet data of the user includes eating time of the user, food taste or composition, a degree of satiety, and the like. The exercise data of the user includes exercise time, duration, exercise intensity, exercise frequency, and the like of the user. The sleep data of the user includes a sleep time period, sleep duration, deep sleep or not, a deep sleep time period, deep sleep duration, and the like of the user. The physical symptom data includes whether the user has a physical symptom related to diabetes, for example, polyuria, polydipsia, polyphagia, and unintended weight loss. The drug use data of the user includes whether a drug is used, a drug type, a drug use frequency, and the like. In some descriptions of embodiments of this application and the accompanying drawings, the physical symptom data and the drug use data are described as health data. The second data may further include a psychological pressure index, an emotion index, and the like, and indicates a magnitude of recent psychological pressure of the user, whether the user is in a good mood, and the like.

The following uses an example in which the method provided in this embodiment of this application is applied to a system including a wearable device and a mobile phone for description.

In some embodiments of this application, the mobile phone receives a trigger operation of performing diabetes risk detection by the user. In response to the trigger operation, the mobile phone obtains the second data, and the mobile phone obtains the first data via the wearable device. Then, the mobile phone detects, based on the first data and the second data, the diabetes risk of the user, to obtain the diabetes risk detection result.

As described above, the first data includes any data that can reflect a diabetes feature and that is further used for diabetes risk detection. The second data includes at least one of the following: the basic information, the diet data, the exercise data, the health data, the sleep data, and the like of the user.

The trigger operation of performing diabetes risk detection by the user is used to trigger the mobile phone to enable a diabetes risk detection function. Optionally, the mobile phone provides, for the user by using an application, for example, an application "Health", an entry for enabling the diabetes risk detection function. For another example, the mobile phone provides the entry of the function for the user by using an "applet". For another example, the mobile phone provides the entry of the function for the user by using a recommended service of a service widget. In this case, the trigger operation of performing diabetes risk detection by the user may be a series of operations such as tapping and sliding in the application, the applet, or the service widget. Optionally, the trigger operation may alternatively be a shortcut operation of the user, for example, a shortcut operation performed through a gesture or a combination of buttons, or the like. The trigger operation may alternatively be a voice command entered by the user, for example, invoking a voice assistant to enable the diabetes risk detection function. A specific implementation form of the trigger operation is not limited in this embodiment of this application.

Figures 1, 4A:
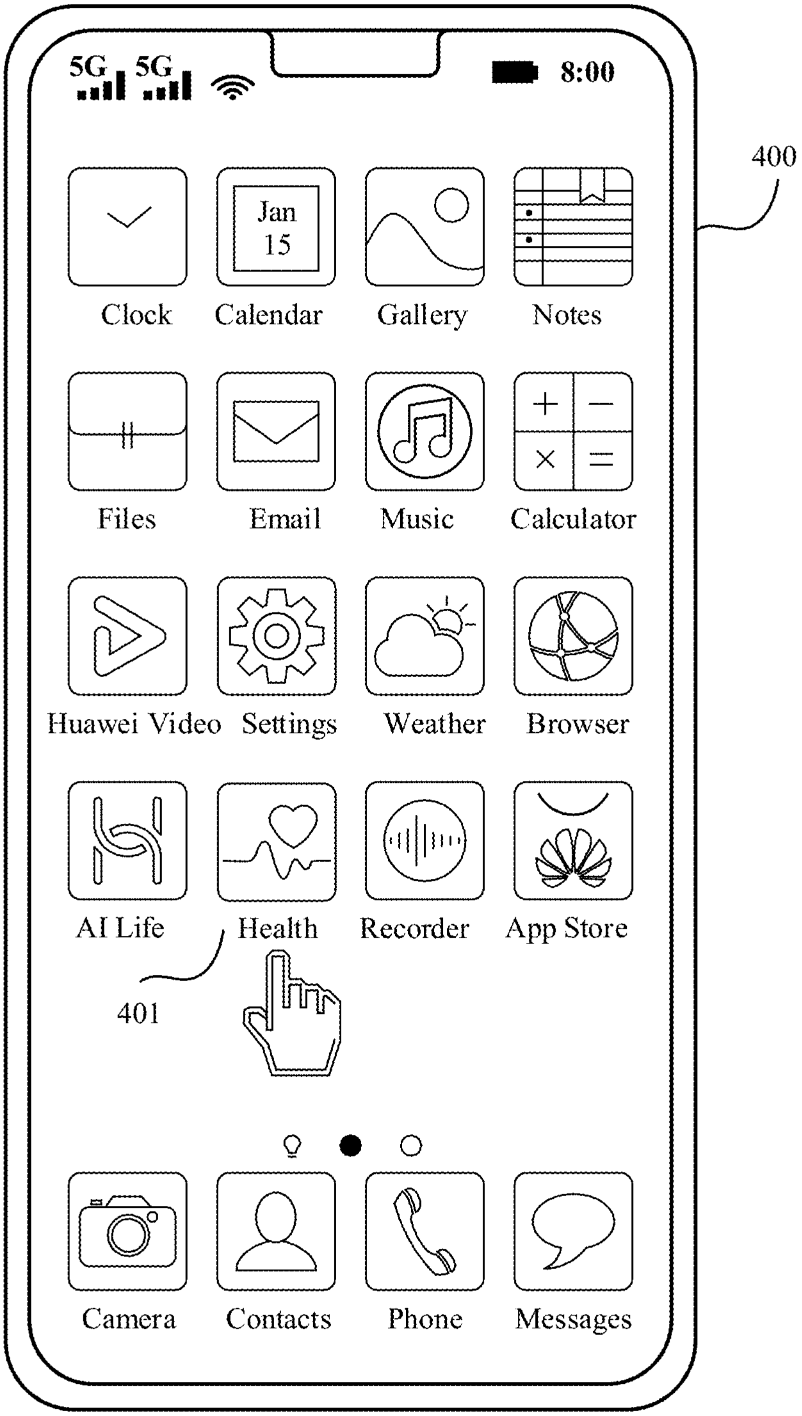
Figures 2, 4A:
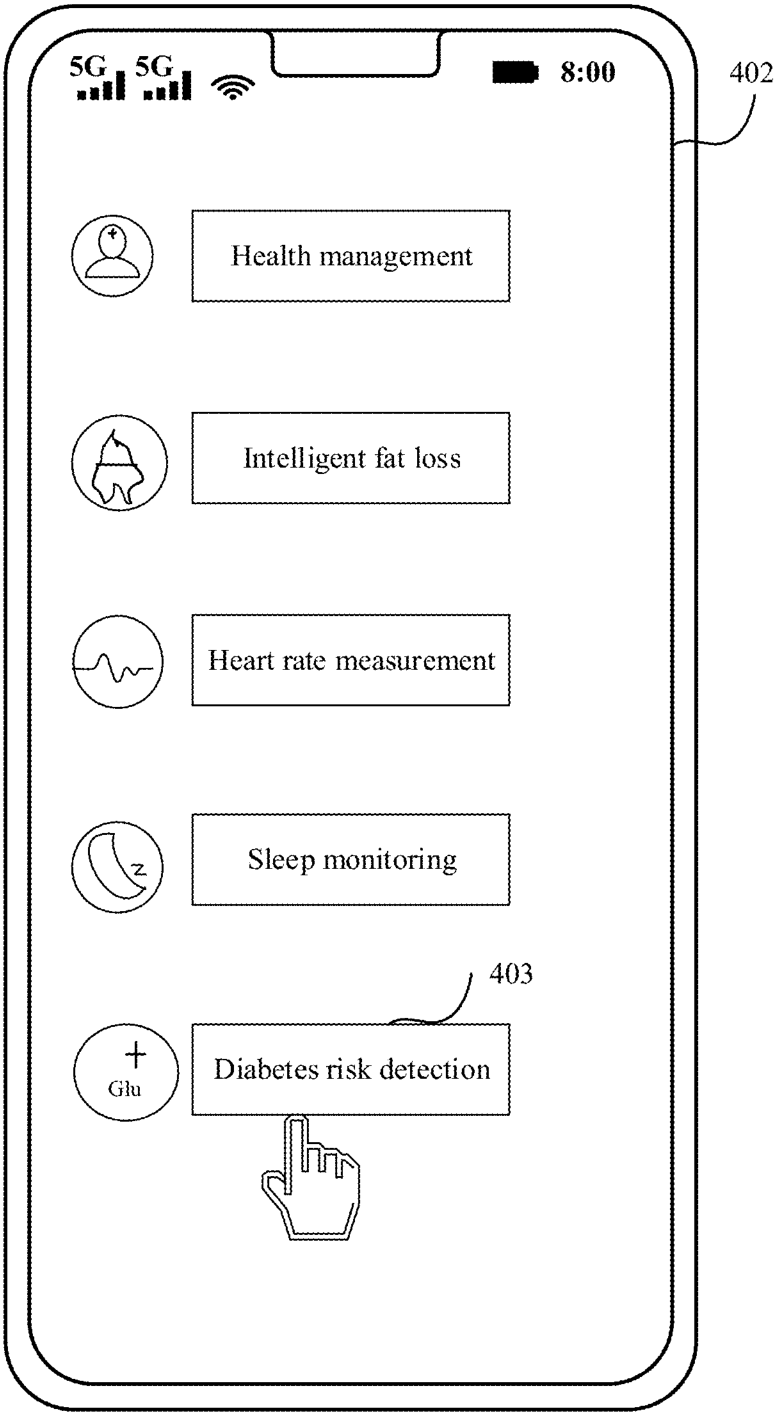

For example, as shown in FIG. 4A-1, an application 401 "Health" is installed on a home screen 400 of the mobile phone. The user taps an icon of the application, and the mobile phone displays an interface 402 shown in FIG. 4A-2. The interface 402 displays icons of all functional modules that can be provided by the application, such as icons of functional modules such as health management, intelligent fat loss, heart rate measurement, sleep monitoring, and diabetes risk detection. If the user taps an icon 403 of the functional module "diabetes risk detection" in the application, the mobile phone jumps to an interface 404 shown in FIG. 4B-1, and displays, on the interface 404, specific functions provided by the module, such as two functions: "long-term detection" and "short-term detection".

The "long-term detection" and the "short-term detection" are distinguished based on a time length of the collected first data during diabetes risk detection. Time of the collected first data for "long-term detection" is long, and is usually five to seven days. Time of the collected first data for "short-term detection" is short, and is usually one or two days. Correspondingly, a detection result corresponding to "long-term detection" is more accurate than a detection result corresponding to "short-term detection", and time for the user to wait for the result is also longer. The foregoing five to seven days and one or two days are merely examples for description, and are intended to distinguish between a time length of first data needs to be collected for long-term detection and a time length of first data needs to be collected for short-term detection. Specific duration is determined based on an actual function of the electronic device. Optionally, descriptions of the two functions are provided for the user in the interface 404, so that the user selects a detection function that meets a requirement of the user. Regardless of whether the user selects the function of "short-term detection" or "long-term detection", it is equivalent to that the user performs the trigger operation of diabetes risk detection. Optionally, in another possible implementation, the "short-term detection" function and the "long-term detection" function are not distinguished in the function provided by the functional module "diabetes risk detection". In other words, the module may provide only one default detection function. Provided that the mobile phone detects that the user triggers the function, the mobile phone obtains the first data and the second data that are used for diabetes risk detection.

The method in this embodiment of this application may be applied to both a short-term detection scenario and a long-term detection scenario, to improve accuracy of the detection result. The following uses an example in which the user selects the "short-term detection" function for description.

Figures 1, 4B:
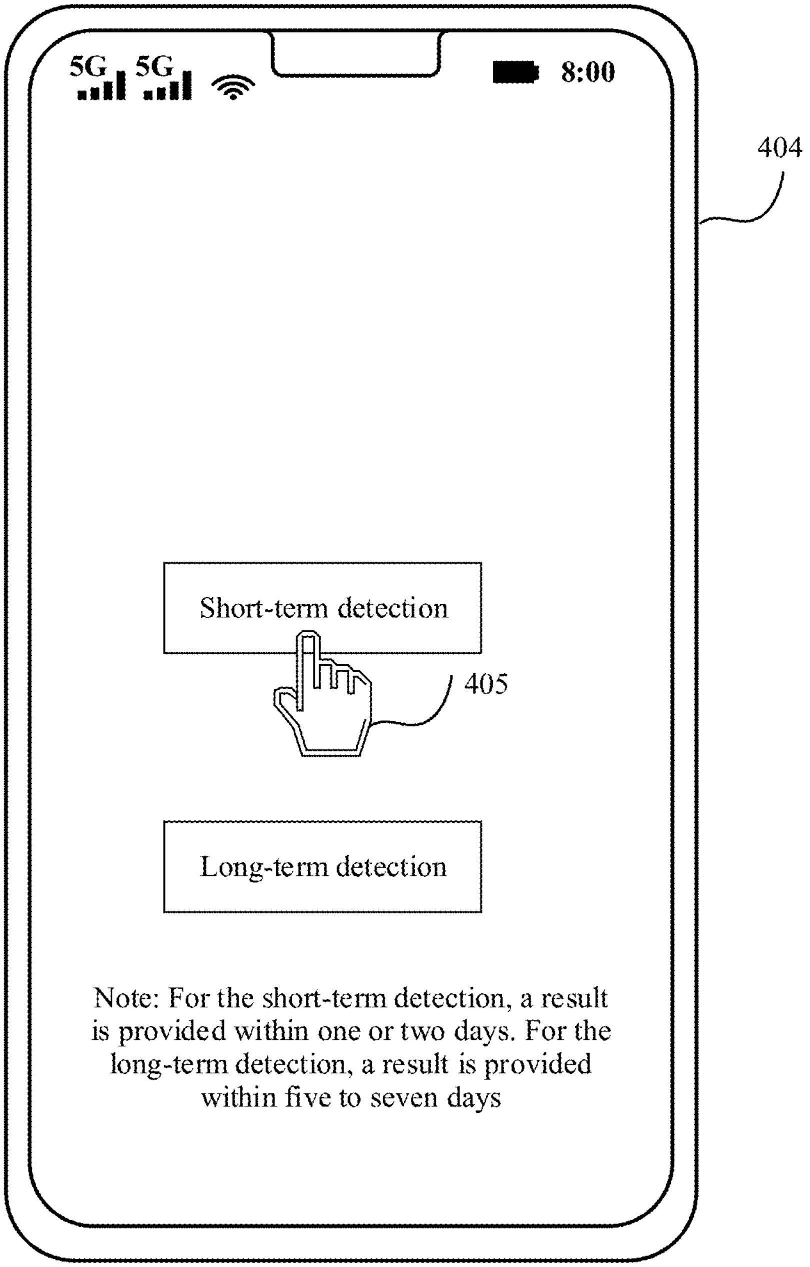
Figures 2, 4B:
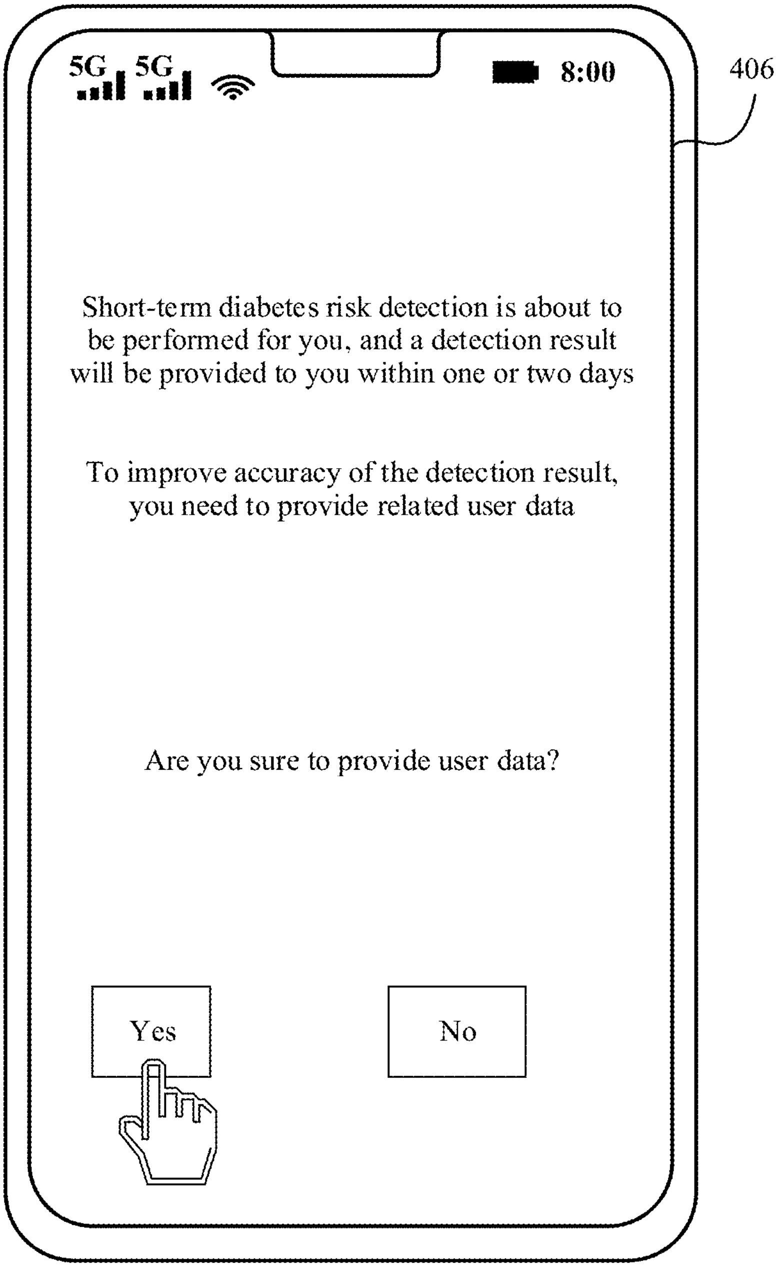
Figures 3, 4B:
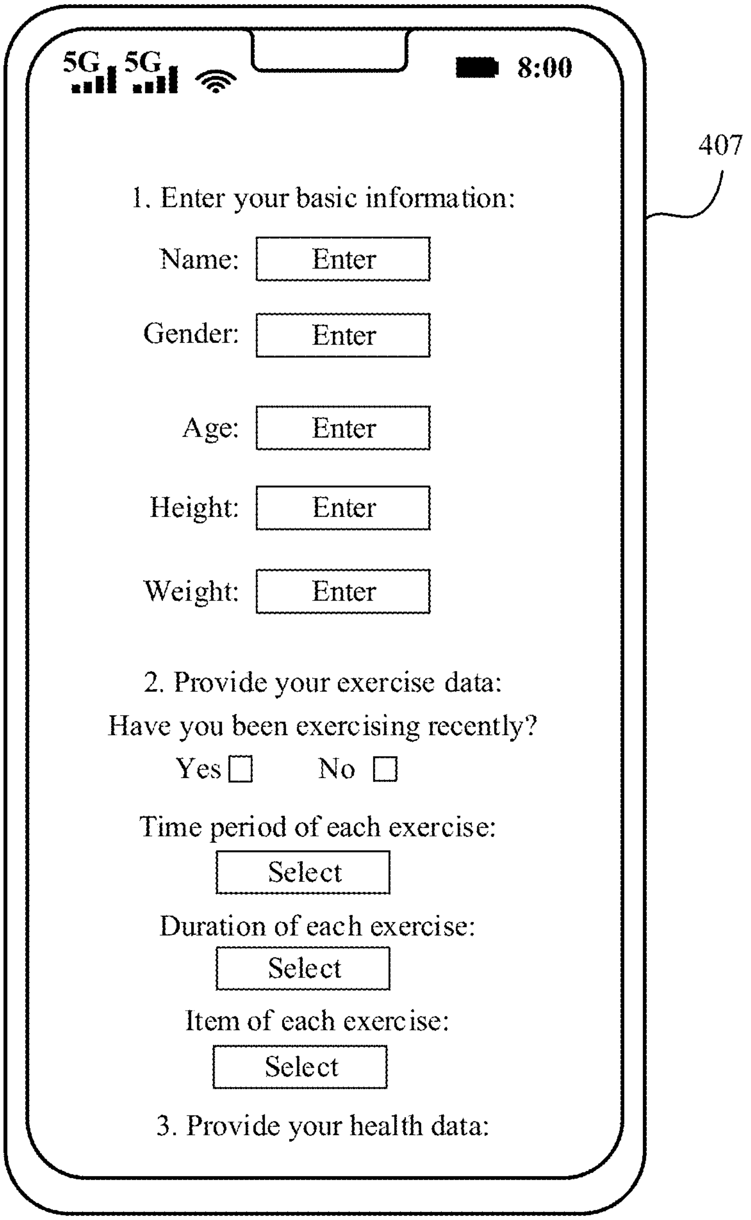

For example, as shown in FIG. 4B-1, after detecting an operation 405 of selecting the "short-term detection" function by the user, the mobile phone obtains the first data and the second data that are used for diabetes risk detection.

Optionally, the mobile phone may obtain the second data through interacting with the user. For example, the mobile phone displays a prompt interface 406 shown in FIG. 4B-2. In the prompt interface 406, the mobile phone displays prompt information used to collect the second data. For example, the following message is displayed: "Short-term diabetes risk detection is about to be performed for you, and a detection result will be provided to you within one or two days. To improve accuracy of the detection result, you need to provide related user data. Do you provide user data?" Corresponding selection controls "Yes" and "No" for the user to select whether to provide the user data are displayed.

If the user selects "Yes" in the prompt interface 406, the mobile phone displays an interface 407 shown in FIG. 4B-3, and the second data that needs to be provided by the user is displayed in the interface 407. The second data can reflect a daily life habit of the user. Content of the second data may cover all aspects of the daily life habit of the user. More types and more detailed content of the second data that can be provided by the user can improve accuracy of the detection result.

For example, the interface 407 displays the second data related to personal information, the exercise data, the health data, and the diet data that the user needs to provide. The personal information specifically includes a gender, an age, a height, a weight, and the like of the user. The exercise data includes an exercise time period, exercise duration, an exercise item, and an exercise frequency (for example, a quantity of exercise times in a preset time period, like three times a week or two times a month) of the user. The health data includes physical symptom data, drug use data, and the like. The diet data includes a latest diet type (for example, light, oily, or sweet) of the user and a degree of satiety (the degree of satiety refers to that whether the user feels hungry or full after eating, like 50% satiety, 80% satiety, or 100% satiety). It may be understood that only some examples of the second data that needs to be provided by the user are provided in the interface 407. In an actual design, more or less second data that needs to be provided by the user may be included.

In a possible implementation, all second data that needs to be filled in by the user is displayed on a same page. However, if the user needs to fill in a large amount of second data and a current page cannot completely display all the second data, the user may scroll the page to display the complete second data. In a possible implementation, all the second data that needs to be filled in by the user is separately displayed on different pages. For example, the personal information, the exercise data, the health data, and the diet data of the user are separately displayed on four different pages. The user can turn pages or tap prompt information at the bottom of the page, for example, "Next" to turn to a next page. If the user does not want to provide some second data, the user does not need to fill in the corresponding data or tap "Skip". For example, after filling in the second data, the user may tap a button like "Submit" to submit filled-in user data to the mobile phone (a display interface in which the user submits the second data after filling in the second data is not shown in the figure). In another possible implementation, the second data is obtained through voice interaction between the mobile phone and the user. In conclusion, a manner of interaction between the mobile phone and the user when the mobile phone obtains the second data is not limited in this embodiment of this application.

Optionally, the mobile phone may alternatively obtain the second data in another manner, for example, obtain the second data via the wearable device or data that has been entered by the user in another application on a premise that authorization from the user is obtained. For example, in the prompt interface 406, after the user selects "Yes", the mobile phone displays a prompt interface. The prompt interface may include the following content: "Your exercise data will be obtained via the wearable device" and corresponding controls "Agree" and "Disagree"; and/or "Your sleep data will be obtained via the sleep detection module in the Health application" and corresponding controls "Agree" and "Disagree"; and/or "Your diet data will be obtained via the diet management module in the Health application" and corresponding controls "Agree" and "Disagree"; and/or "Your health information will be obtained via the health management module in Health" and corresponding controls "Agree" and "Disagree". The user may select "Agree" or "Disagree" for prompt information corresponding to each piece of second data. For prompt information corresponding to a piece of second data, if the user selects "Agree", the mobile phone may obtain corresponding second data from a corresponding application or module. If the user selects "Disagree", the mobile phone may further display a prompt interface similar to the interface 407, to prompt the user to enter corresponding second data.

The mobile phone may separately obtain different pieces of second data via one or more wearable devices. For a manner in which the mobile phone establishes a connection to the wearable device and obtains data like the exercise data and heart rate data via the wearable device, refer to the conventional technology. Details are not described in this application.

In addition, the user may further enter, based on an actual situation, other supplementary second data that the user wants to enter, and the mobile phone may obtain, in a manner like identifying a keyword, the supplementary second data of the user.

In conclusion, in this embodiment of this application, provided that the mobile phone can obtain the second data, a specific implementation in which the mobile phone obtains the second data is not limited.

Figure 4C:
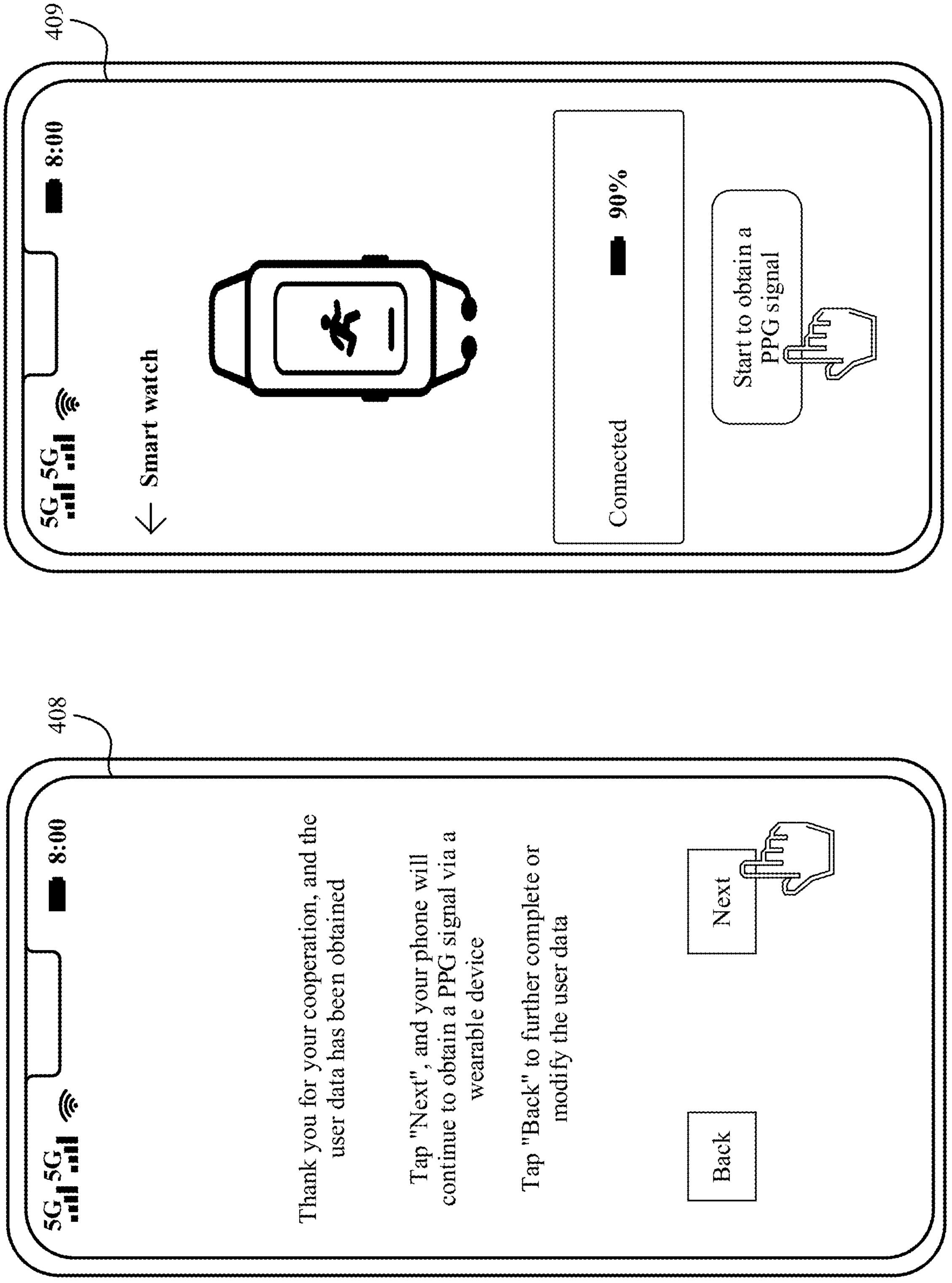
FIG. 4C is a diagram 3 of interfaces according to an embodiment of this application.

After the mobile phone obtains the second data, as shown in an interface 408 in FIG. 4C, the user is prompted that the mobile phone further obtains the first data (a PPG signal is used as an example in the figure) from the wearable device (a smart watch is used as an example in the figure). After the user performs authorization, as shown in an interface 409 in FIG. 4C, the user is prompted with related information of the wearable device. The user may tap "Start to obtain the PPG signal" to indicate the mobile phone to obtain the PPG signal via the smart watch.

Optionally, the example in the foregoing figure is described by using an example in which the mobile phone first obtains the second data and then obtains the first data. In actual application, the mobile phone may first obtain the first data and then obtain the second data, or obtain the first data and the second data simultaneously. Correspondingly, a user interface corresponding to this data obtaining manner is designed for the wearable device and the mobile phone. For example, in another possible implementation, after the user taps "Short-term detection" in the interface 404, the mobile phone obtains the first data via the wearable device (this process may be an internal operation of the mobile phone, to be specific, invisible to the user), and displays the interface shown in the interface 406. A sequence in which the mobile phone obtains the second data and the first data is not limited in this embodiment of this application.

Then, the mobile phone analyzes the obtained second data and the first data obtained via the wearable device, to obtain the diabetes risk detection result of the user. For example, the wearable device is a smart watch. A PPG sensor may be built in the smart watch, a pulse signal is obtained via the sensor, and the pulse signal is analyzed to obtain a PPG signal. The smart watch sends the PPG signal to the mobile phone. The mobile phone obtains the diabetes risk detection result based on the PPG signal and the obtained second data.

Optionally, the mobile phone first obtains a preliminary diabetes risk value (for ease of description, the preliminary diabetes risk value is described as a first risk value in this application) based on the first data (the PPG signal), and then obtains a final diabetes risk value (for ease of description, the final diabetes risk value is described as a second risk value in this application) based on the obtained second data and the first risk value. The second risk value is used as the final diabetes risk detection result.

Optionally, the first risk value is adjusted based on the second data, to obtain the second risk value.

In a possible implementation, the second risk value is obtained based on the first risk value and weights corresponding to different second data. For example, the first risk value is adjusted based on the weights corresponding to the different second data, to obtain the second risk value. A weight corresponding to one piece or one type of second data indicates a degree of impact of the second data on the detection result. A larger degree of impact of one piece or one type of second data on the detection result indicates a larger corresponding weight, and correspondingly, has a larger adjustment amplitude for the first risk value. The weight may be preset. In other words, the first risk value is increased or decreased based on degrees of impact of different second data on diabetes. If one piece or one type of second data has large impact on diabetes, a corresponding adjustment amplitude is large. Correspondingly, if one piece or one type of second data has small impact on diabetes, a corresponding adjustment amplitude is small. For example, first risk values corresponding to diabetes with different risks are set based on a risk level that the user suffers from diabetes. A higher risk level that the user suffers from diabetes indicates a larger corresponding first risk value. For example, it is set that a first risk value corresponding to a user without diabetes (a healthy user) is less than 60 points, a first risk value corresponding to a user in pre-diabetes is 60 points to 80 points, and a first risk value corresponding to a user with diabetes is 80 points to 100 points. If the first risk value obtained by the mobile phone based on the PPG signal is 65 points, the mobile phone analyzes the basic information of the user, and determines that the weight of the user is 65 kg and 158 cm. In this case, the weight of the user is heavy. Because the weight has slight impact on diabetes, the first risk value may be slightly increased, for example, increased by 3 points to 68 points. Further, the mobile phone analyzes the diet data of the user, and determines that the user often eats sweet food recently. Because a diet habit has greater impact on diabetes than the weight, the first risk value is further finely adjusted, for example, increased by 5 points to 73 points. Further, the mobile phone analyzes the exercise data of the user, and determines that the user exercises regularly. Because exercise helps reduce the risk of diabetes, the first risk value is reduced by 3 points to 70 points. Further, the mobile phone analyzes the physical symptom data and the drug use data of the user, and determines drug use and a current physical symptom of the user. If there is a symptom that is closely related to diabetes, the first risk value is increased by 8 points to 78 points because the body symptom data and the drug use data each have great impact on diabetes. Further, the mobile phone may further analyze other second data that can be obtained, for example, the sleep data, high mental pressure or not, and a good mood or not, and sequentially adjust the score, to obtain the second risk value. The second risk value is used as the final diabetes risk detection result. It may be understood that, in addition to analyzing impact of different second data on the diabetes risk, the risk value is sequentially adjusted based on the first risk value. Alternatively, a total adjustment value may be obtained by analyzing impact of different second data on the diabetes risk, and then adjustment is performed based on the first risk value and the total adjustment value, to obtain the second risk value.

In another possible implementation, adjustment amplitudes corresponding to different first data are the same, that is, no weight may be set for the first data. Alternatively, different first data has corresponding preset adjustment values, and adjustment may be performed based on the preset adjustment values. Preset adjustment values corresponding to the different first data may be the same or may be different.

If the user selects "No" in the prompt interface 406, it indicates that the user does not want to provide the second data. In this case, the mobile phone obtains the diabetes risk detection result based on only the first data obtained from the wearable device, that is, the first risk value is used as the diabetes risk detection result.

Figure 4D:
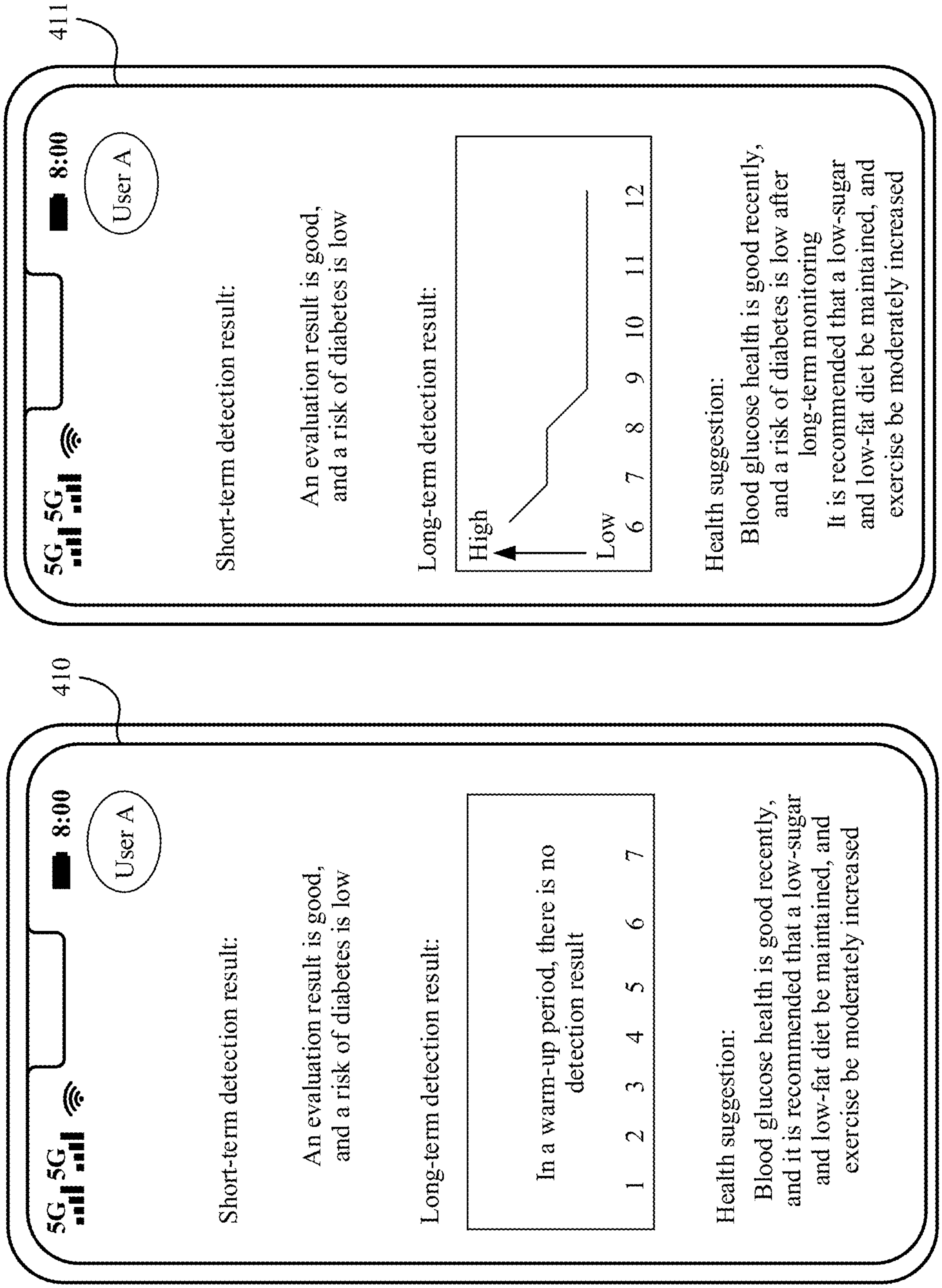
FIG. 4D is a diagram 4 of interfaces according to an embodiment of this application.

Then, the mobile phone outputs the diabetes risk detection result. Usually, the mobile phone displays the diabetes risk detection result on a display interface. The mobile phone may alternatively output the detection result in another manner like voice broadcast. For example, the mobile phone displays the diabetes risk detection result on the display interface. In a possible implementation, if the mobile phone can obtain the second data, the detection result is obtained through comprehensive analysis based on the second data and the first data. In this case, the mobile phone directly displays the second risk value as the diabetes risk detection result. If the second data cannot be obtained, the detection result is obtained through analysis based on the first data, and the mobile phone directly displays the first risk value as the diabetes risk detection result. In another possible implementation, a rough diabetes risk assessment result is obtained based on the diabetes risk value. For example, if the diabetes risk value is less than 60 points, a corresponding assessment result is "An assessment result is good, and a diabetes risk is low". If the diabetes risk value is 60 to 80 points, a corresponding assessment result is "An assessment result is average, and you may be in pre-diabetes and have a risk of diabetes". If the diabetes risk value is 80 to 100 points, a corresponding assessment result is "An assessment result is poor, and you have an extremely high risk of diabetes". The mobile phone displays the rough diabetes risk assessment result. For example, as shown in an interface 410 in FIG. 4D, an evaluation result that "An evaluation result is good, and a risk of diabetes is low" is displayed in the interface.

Optionally, regardless of a manner in which the diabetes risk detection result is output, the mobile phone may further output a description and a health suggestion that correspond to the detection result. For example, if the assessment result is "An assessment result is good, and a diabetes risk is low", a corresponding description may be "Assessment results are classified into good, average, and poor based on the PPG signal and the user data that are obtained by the wearable device. Your current assessment result is good, indicating that a blood glucose concentration is maintained at a good level". For example, as shown in the interface 410, a health suggestion corresponding to the evaluation result may be: Blood glucose health is good recently, and it is recommended that a low-sugar and low-fat diet be maintained, exercise be moderately increased, and the like.

Optionally, if the "diabetes risk detection" module provides two functions: "short-term detection" and "long-term detection", both a short-term detection result and a long-term detection result may be output.

For example, both the short-term detection result and the long-term detection result are displayed on a same interface. Because time for collecting the second data is longer for the long-term detection result, a case that may occur in the display interface is as follows: The short-term detection result is output, but the long-term detection result is still in a warm-up period and not output. For example, as shown in the interface 410 in FIG. 4D, "Short-term detection result: An evaluation result is good, and a diabetes risk is low" and "Long-term detection result: In a warm-up period, there is no detection result" are displayed on the interface.

The warm-up period may be understood as a time period for waiting for the long-term detection result, or a time period from a time point at which the first data starts to be collected to a time point at which the long-term detection result is obtained.

If the first data is collected for a long time, a case that may occur in the display interface is that there are both the short-term detection result and the long-term detection result. For example, as shown in an interface 411 in FIG. 4D, the short-term detection result is displayed in the interface: An evaluation result is good, and a diabetes risk is low. A long-term detection result expressed in an image is also displayed.

As described above, in an existing diabetes risk detection solution, accuracy of the detection result obtained based on only the first data is low because the collected first data is insufficient for "short-term detection". However, in this embodiment of this application, the second data is collected, and comprehensive analysis is performed based on the second data and the first data. This is equivalent to that the diabetes risk detection result obtained based on the first data is calibrated by using the second data, to obtain a calibrated diabetes risk detection result. This improves accuracy of the detection result.

In addition, compared with "long-term detection", a detection result of a diabetes risk in a shorter time can be quickly provided in the solution provided in this embodiment of this application. This relieves anxiety of the user in a waiting process, and the detection result can reflect a diabetes risk status of the user in a short time, to meet a requirement of the user and improve user experience.

Figure 5:
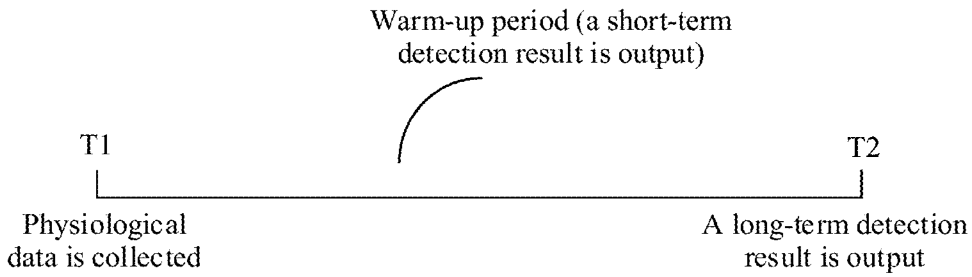
FIG. 5 is a diagram of a warm-up period according to an embodiment of this application.

For example, as shown in FIG. 5, $T_1$ is a moment at which the first data starts to be collected, and $T_2$ is a moment at which the long-term risk detection result is obtained by collecting the first data for a long time. The warm-up period is between $T_1$ and $T_2$. If "long-term detection" is used, the user needs to wait until the moment $T_2$ to obtain the long-term detection result. If "short-term detection" is used, the user can obtain the short-term detection result at a moment between $T_1$ and $T_2$, and accuracy of the detection result is high because the detection result is calibrated based on the second data.

Optionally, in this embodiment of this application, the mobile phone may further determine confidence of the detection result, that is, reliability or accuracy of the detection result, based on the collected second data and the collected first data. Duration of the collected the first data, quality of the collected first data, a type of the collected second data, a detail level of the collected second data, and the like affect the confidence of the detection result. The quality of the collected first data may be obtained by determining whether the first data is missing, a user status, and the like. For example, if the first data of the user at important time like time of three meals and nap time is not collected, the quality of the first data is poor. For another example, the first data may be affected by an exercise status of the user. If the first data is collected when the user performs a violent activity, the quality of the first data is poor.

Longer duration and higher quality of the collected first data, more types of the collected second data, and more detailed second data indicate higher confidence of the detection result. In other words, when the same first data is collected, more types and more detailed of second data that can be obtained by the mobile phone indicate higher confidence of a detection result corresponding to the second data.

For example, for a same user, if a diabetes risk of the user in last three days needs to be detected, if the first data that can be obtained includes a PPG signal of the user in the last three days, and the obtained second data includes only basic information and diet data of the user, an obtained detection result is a first detection result. If the first data that can be obtained includes the PPG signal of the user in recent three days, and the obtained second data includes the basic information, the diet data, the physical symptom data, the drug use data, and the exercise data of the user, an obtained detection result is a second detection result. In this case, confidence of the second detection result is higher than confidence of the first detection result.

Figure 6A:
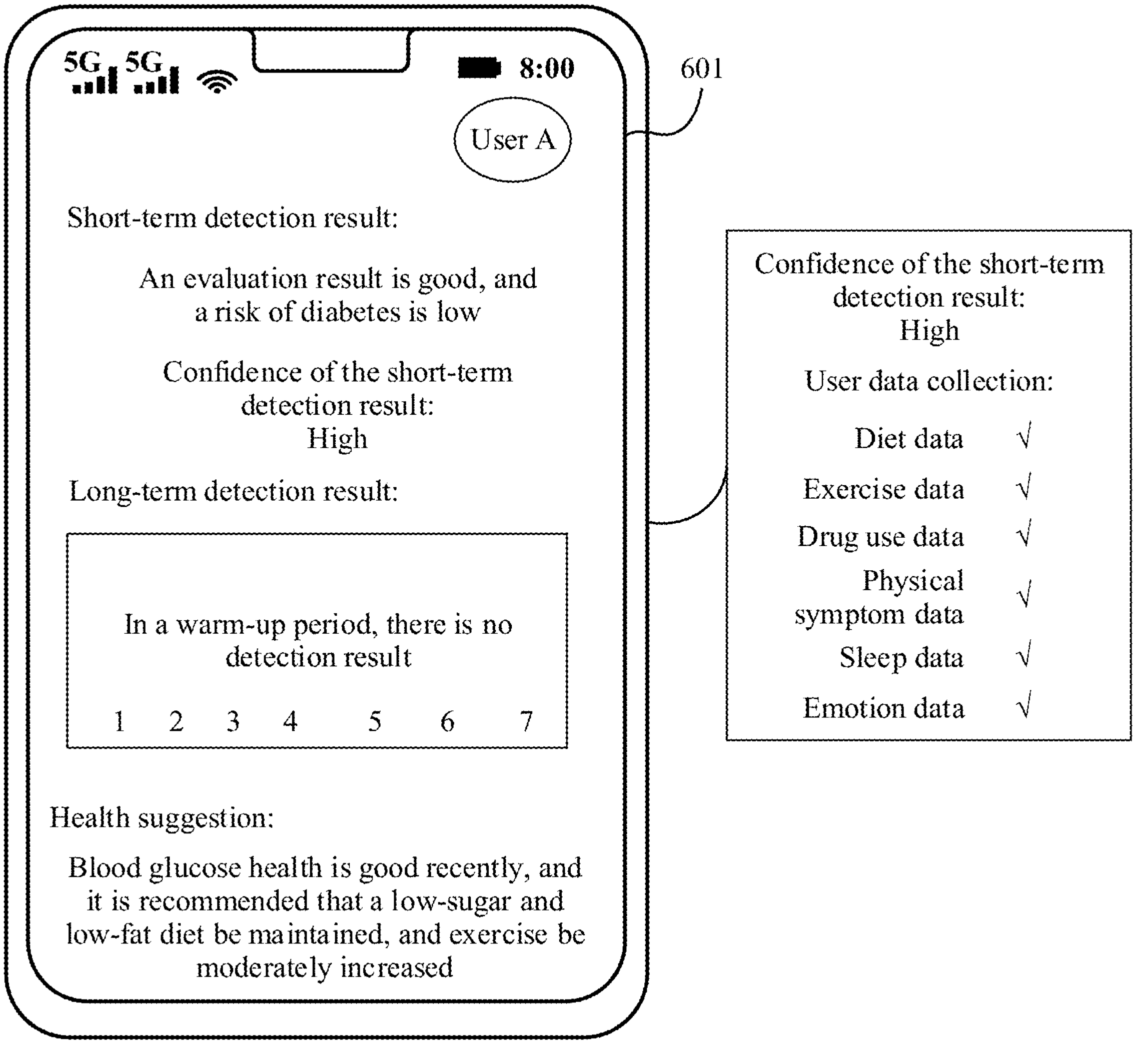
FIG. 6A is a diagram 5 of an interface according to an embodiment of this application.
Figure 6B:
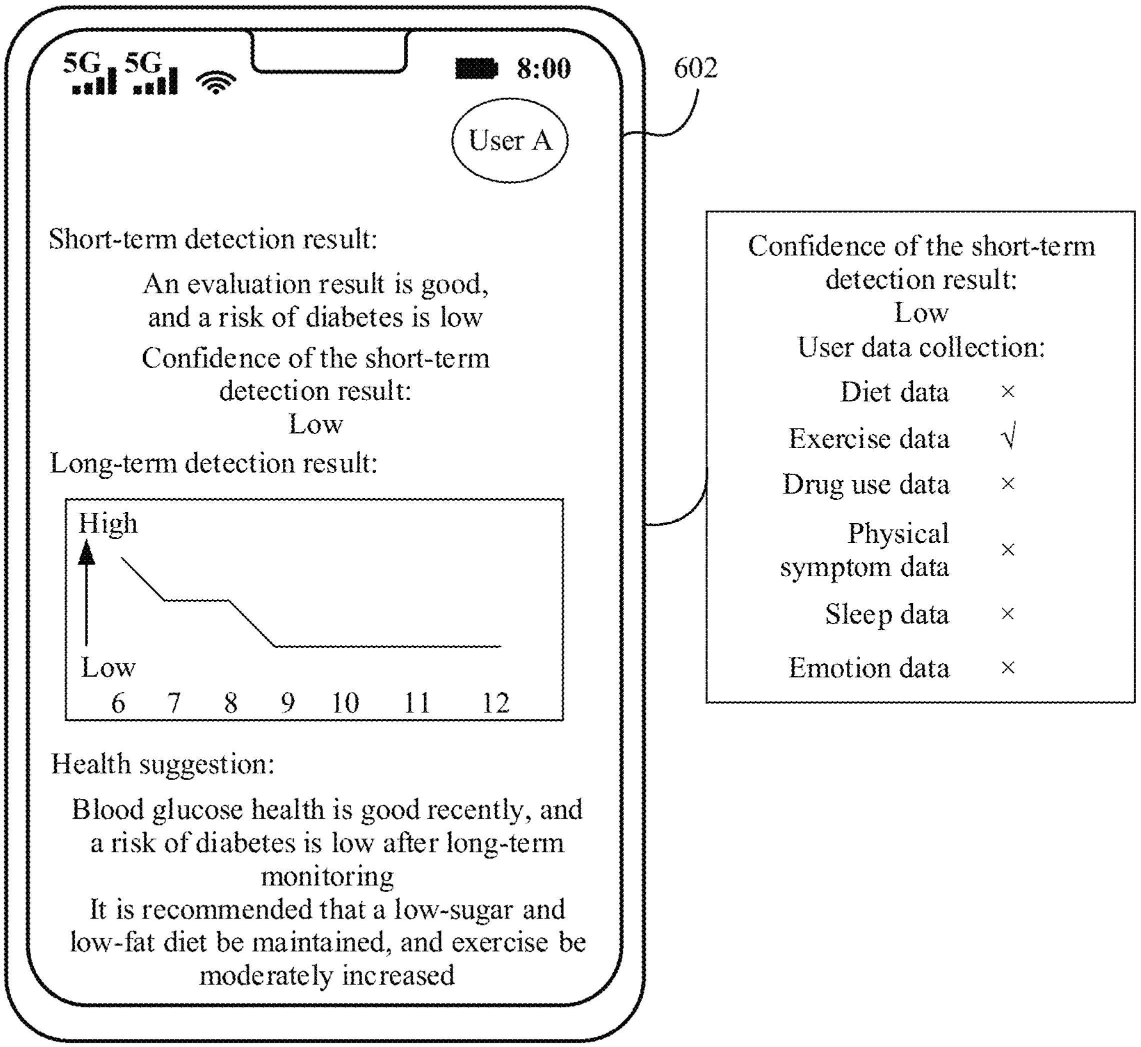
FIG. 6B is a diagram 6 of an interface according to an embodiment of this application.

Optionally, the mobile phone outputs not only the detection result, but also the confidence of the detection result. For example, in an interface 601 shown in FIG. 6A and an interface 602 shown in FIG. 6B, a diabetes risk detection result and confidence corresponding to the detection result are displayed in each of the interface 601 and the interface 602. The confidence is usually represented by a probability. In this embodiment of this application, after a probability value is calculated, an interval range in which the probability value is located is obtained based on a value of the probability value. Different interval ranges correspond to a rough confidence high-low status, and then the confidence is displayed as the rough confidence high-low status. For example, a probability value less than 60% corresponds to relatively low confidence, a probability value between 60% and 75% corresponds to low confidence, a probability value between 75% and 90% corresponds to relatively high confidence, and a probability value above 90% corresponds to high confidence. Optionally, the confidence may alternatively be displayed on the interface in a form of a probability value.

In addition, the mobile phone may further prompt the user with an impact relationship between the confidence and the second data, that is, prompt the user with the confidence of the diabetes risk detection result and the second data corresponding to the confidence. As shown in the interface 601, if the user taps the confidence, the second data that can be obtained and that corresponds to the confidence may be further displayed. The second data includes the diet data, the exercise data, the physical symptom data, the drug use data (the physical symptom data and the drug use data further include drug use data and physical symptom data), the sleep data, and the emotion data (for example, high mental pressure). As shown in the interface 602, if the user taps the confidence, the obtained second data corresponding to the confidence is displayed, and includes only the exercise data, and does not include other data. It can be learned that a reason why the confidence shown in the interface 602 is lower than the confidence shown in the interface 601 is that a small amount of second data is obtained in the interface 602.

Optionally, when the confidence is less than a preset threshold, the user is prompted to edit the obtained second data or enter more second data (in this application, more second data that needs to be entered by the user may also be described as third data). In other words, for a detection result with low confidence, the mobile phone may further prompt the user to complete the obtained second data or enter more second data, to improve the confidence of the detection result. For example, the mobile phone may play a voice announcement or display the following message: "Confidence of a current detection result is low. To improve accuracy of the detection result, please provide more user data. After you provide more user data, a detection result will be output for you again". In this way, the confidence of the detection result is improved by continuously guiding the user to enter more second data.

In the foregoing solution, the second data obtained by the mobile phone is all possible second data of the user within a period of time. Generally, in a process of obtaining the second data, interaction with the user is required, and this brings a specific "interaction load" to the user. In addition, the mobile phone determines the detection result based on a large amount of second data, and both a collection amount and a calculation amount of the detection result are large.

To reduce a data volume of the obtained second data, the interaction load of the user and a processing load of the mobile phone are reduced. Optionally, in some embodiments of this application, for some specific time periods, only second data in the specific time periods may be collected.

Optionally, in some embodiments of this application, if it is determined that quality of the collected first data is poor or data is missing in a time period, only the second data is collected in the time period. The first data is collected for a period of time, and statistical analysis is performed on the first data that is within the period of time, to identify a time period in which quality of the first data is poor or data is missing.

For example, a pulse signal of the user within one month is collected, and a time period in which quality of the pulse signal is poor or data is missing is detected based on features such as a waveform and a peak value of the pulse signal. For example, the time period is usually a nap time period of the user. In this case, when obtaining the second data, the mobile phone obtains only the second data of the user in the nap time period.

Figure 7:
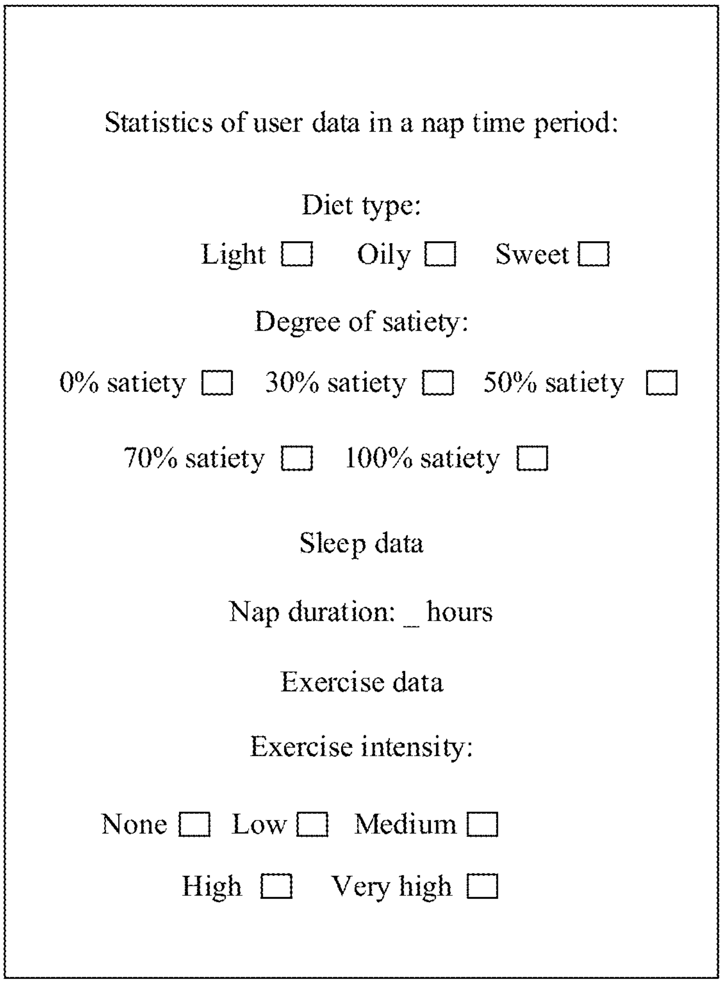
FIG. 7 is a diagram 7 of an interface according to an embodiment of this application.

For example, as shown in FIG. 7, the obtained second data of the user in the nap time period includes a degree of satiety (for example, 0% satiety, 30% satiety, 50% satiety, 80% satiety, 100% satiety, or 120% satiety) of the user for lunch, lunch type (for example, light, oily, and sweet), and exercise data (for example, low exercise intensity, medium exercise intensity, and extremely high exercise intensity).

It may be understood that the second data in the nap time period shown in FIG. 7 is merely an example for description, and the second data in the nap time period is not limited to the data shown in FIG. 7.

Optionally, for some important time periods (for example, a night sleep time period, time periods before and after three meals, and a nap time period), if the first data is missing or quality is poor, accuracy of the detection result is greatly affected. In this case, for these important time periods, the second data of the user in these important time periods is collected. For example, for the night sleep time period, sleep time, sleep duration, and a deep sleep status (for example, deep sleep or not, a deep sleep time period, and deep sleep duration) of the user are obtained. For the time periods before and after the three meals, a degree of satiety, a diet type, exercise data, and the like of each of the three meals of the user are separately obtained. For the nap time period, nap time, nap duration, and the like of the user are obtained.

Optionally, for the important time periods, statistics collection is performed on only first data in these important time periods, to determine a time period in which quality of the first data is poor or data is missing in the important time periods. For example, statistics collection is performed on first data in the night sleep time period, the time periods before and after three meals, and the nap time period, to identify whether the user has a time period in which quality of the first data is poor or data is missing in these important time periods. If only the second data of the user in the night sleep time period is missing, the second data of the user in the night sleep time period is separately collected.

Optionally, considering that the first data at night is usually stable, a segment of first data with stable quality may be collected during the sleep period of the user, and the first data in this time period has great impact on accuracy of the detection result. Therefore, the mobile phone collects the second data that is within the sleep time period, including information such as time to fall asleep, a diet before bed, and whether the user exercises before bed, to further eliminate interference caused by various behaviors of the user before bed to the detection result, to improve accuracy of the detection result.

In a possible implementation, the mobile phone determines, based on data collected by the wearable device, for example, ACC data and a heart rate, an activity status of the user at common sleep time, and further determines whether there is a possibility of an activity like staying up late, eating, or exercising. If the user has an activity like staying up late, eating, or exercising, the mobile phone interacts with the user to collect information like diet and exercise of the user before bedtime.

In another possible implementation, regardless of whether the wearable device can collect the activity status of the user, the mobile phone collects the second data that is within the sleep time period in a targeted manner.

In this way, data in different time periods has different importance to a detection algorithm, an important data segment (for example, the night sleep time period, the time periods before and after three meals, or the nap time period) greatly affects confidence of the detection result when signal quality is poor or signal is missing. According to the foregoing method provided in this embodiment of this application, on a premise of reducing the user interaction load as much as possible, targeted information collection is separately performed on the important data segment in which signal quality is poor or signal is missing, so that accuracy of the detection result can be improved.

Optionally, a difference between the second data obtained by the mobile phone causes a difference in the confidence of the detection result. Some data has large impact on the confidence of the detection result. In this case, the mobile phone may obtain only the data, and the confidence of the detection result obtained based on the second data and the first data can meet a requirement. However, some data has small impact on the confidence of the detection result. In this case, the mobile phone needs to obtain a large amount of second data, so that the confidence of the detection result can meet the requirement.

In this embodiment of this application, priorities of different second data are obtained based on a degree of impact of the second data on the confidence of the detection result. In this case, the mobile phone may collect the second data based on the priorities, and after collecting second data with a high priority, determine a detection result and confidence of the detection result based on the second data with the high priority and the first data. If the confidence meets the requirement, the second data does not need to be further collected. If the confidence does not meet the requirement, second data of a next priority is further collected.

In other words, it is assumed that the second data includes a plurality of types of second data. In this case, the first data is obtained, and the second data is obtained in descending order of the priorities of different second data. After the second data is obtained each time, if it is determined, based on the obtained second data and the obtained first data, that the confidence of the obtained diabetes risk detection result is greater than or equal to the preset threshold, obtaining of the second data is stopped. Otherwise, if it is determined, based on the obtained second data and the obtained first data, that the confidence of the obtained diabetes risk detection result is less than the preset threshold, the second data continues to be obtained until the confidence of the diabetes risk detection result is greater than or equal to the preset threshold. In other words, the first data may be obtained, and the second data with the high priority is obtained based on the priorities of different second data. If it is determined, based on the second data with the high priority and the first data, that the confidence of the obtained diabetes risk detection result is greater than or equal to the preset threshold, obtaining of the second data is stopped. If it is determined, based on the second data with the high priority and the first data, that the confidence of the obtained diabetes risk detection result is less than the preset threshold, second data with a low priority is obtained, and the diabetes detection result is determined based on the obtained second data and the obtained first data until the confidence of the diabetes risk detection result is greater than or equal to the preset threshold.

Optionally, the mobile phone may perform training via a neural network model, to obtain the priorities of different second data. In a possible implementation, general priorities of the second data are obtained through training or are set, and the general priorities are applicable to all users. In a possible implementation, for different users or different groups, priorities of different second data may be different. For example, for some users, a priority sequence of the second data is: the physical symptom data>the drug use data>the diet data>the exercise data>the sleep data. For some other users, a priority sequence of the second data is: the physical symptom data>the drug use data>the exercise data>the sleep data>the diet data. In actual application, priorities of second data corresponding to different types of users or different types of users may be separately determined.

Figure 8:
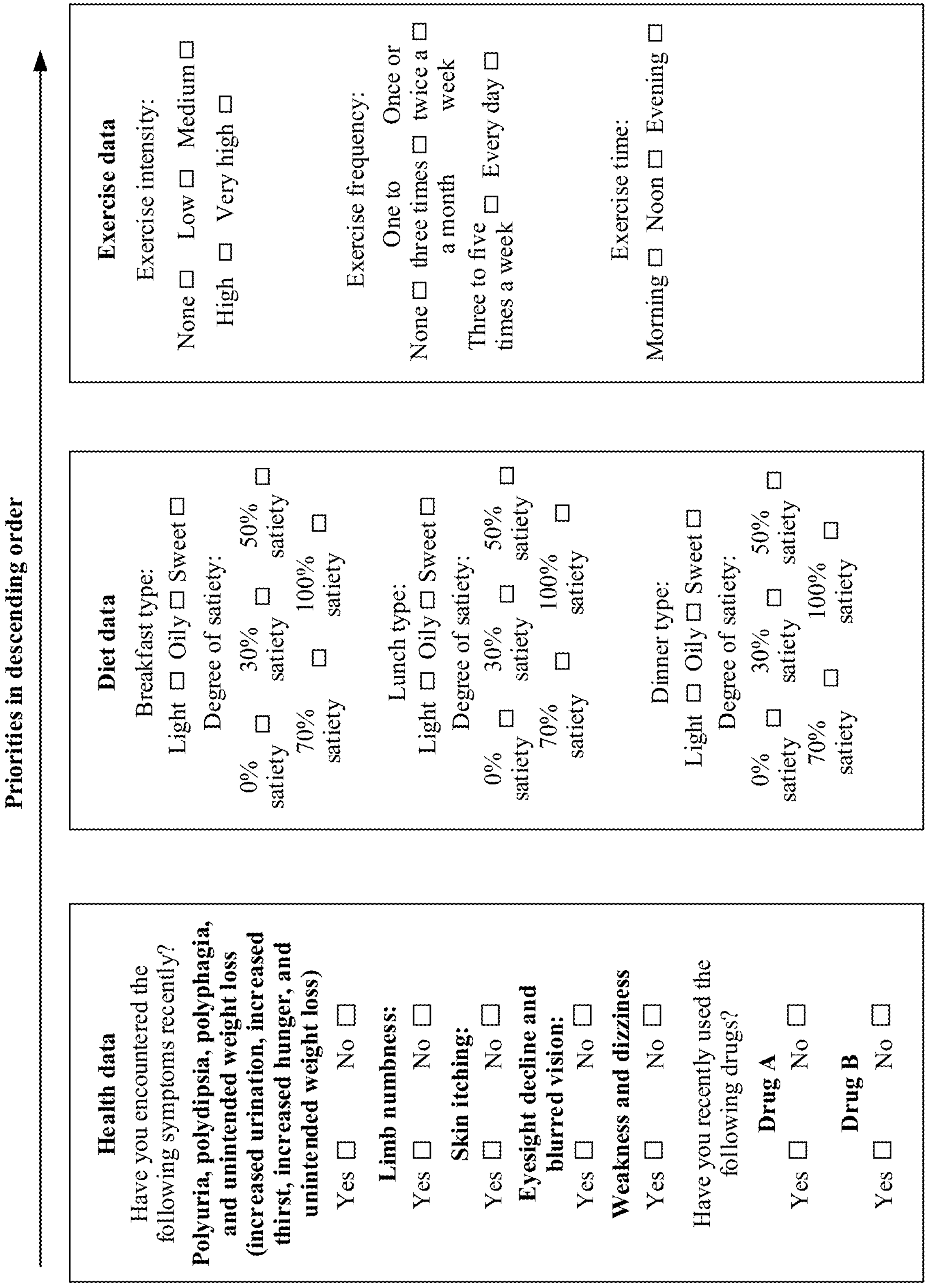
FIG. 8 is a diagram 8 of an interface according to an embodiment of this application.

For example, as shown in FIG. 8, for a user, a priority sequence of different second data corresponding to the user is as follows: the physical symptom data and the drug use data>the diet data>the exercise data>the sleep data. In this case, the mobile phone may first interact with the user to obtain the physical symptom data and the drug use data, and determine a diabetes risk detection result and confidence of the detection result based on the obtained physical symptom data, the obtained drug use data, and the obtained first data. If the confidence is greater than the preset threshold, no other second data needs to be further obtained. On the contrary, if the confidence is less than the preset threshold, the diet data is further obtained according to the priority order. Similarly, if confidence of a detection result determined based on the physical symptom data, the drug use data, the diet data, and the first data is still less than the preset threshold, the exercise data is further obtained. Otherwise, other second data does not need to be obtained. The rest may be deduced by analogy until the confidence of the detection result is greater than the preset threshold, or all possible second data is obtained.

Compared with a case in which the user needs to fill in all the second data at a time, this manner can reduce a data volume of the second data filled in by the user, and reduce an interaction load of the user. For example, it is assumed that the physical symptom data, the drug use data, the diet data, and the exercise data are separately located on different pages. In comparison with a case in which the user turns pages between the three pages and fills in all data on the three pages, in this manner of filling based on the priorities, the user may need to fill in only one type of content (that is, content on one page) of the physical symptom data and the drug use data, and does not need to fill in other second data. This reduces the interaction load of the user.

In this way, according to the method provided in this embodiment of this application, the second data of different priorities is sequentially collected based on the priorities of the second data, and the detection result and the confidence of the detection result are calculated each time the second data is collected. After the confidence meets the requirement, the second data may be stopped from being collected, thereby reducing an "interaction load" of the user.

In some solutions, a plurality of embodiments of this application may be combined, and a combined solution is implemented. Optionally, some operations in the procedures of the method embodiments are optionally combined, and/or a sequence of some operations is optionally changed. In addition, an execution sequence of steps of each procedure is merely an example, and does not constitute a limitation on an execution sequence of the steps. The steps may be alternatively performed in another execution sequence. It is not intended to indicate that the execution sequence is the only sequence in which these operations can be performed. A person of ordinary skill in the art may learn a plurality of manners of re-ranking the operations described in this specification. In addition, it should be noted that process details related to an embodiment in this specification are also applicable to another embodiment in a similar manner, or different embodiments may be used in combination.

In addition, some steps in the method embodiments may be equivalently replaced with other possible steps. Alternatively, some steps in the method embodiments may be optional, and may be deleted in some use scenarios. Alternatively, another possible step may be added to the method embodiments.

In addition, the method embodiments may be implemented separately or in combination.

The foregoing describes in detail the diabetes risk detection method provided in embodiments of this application. The following describes, with reference to the accompanying drawings, a system and an apparatus that can implement the method provided in embodiments of this application.

Figure 9:
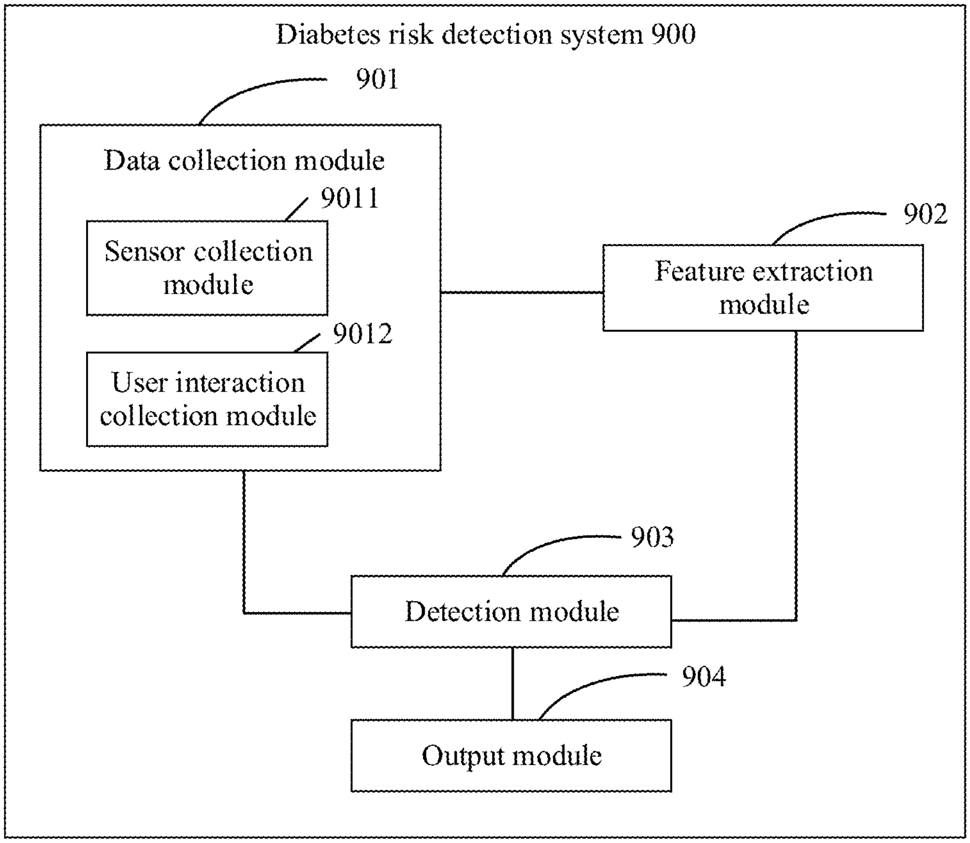
FIG. 9 is a diagram 2 of a structure of a system according to an embodiment of this application.

For example, as shown in FIG. 9, the diabetes risk detection system 900 includes the following modules.

A data collection module 901 is configured to collect first data and second data.

Optionally, based on different collected data, the data collection module may be further divided into a sensor collection module 9011 and a user interaction collection module 9012. The sensor collection module 9011 is configured to collect data collected via a sensor, for example, the first data like PPG and ACC of a user and a part of the second data (the part of the second data includes sleep data, exercise data, and the like).

Optionally, the user interaction collection module 9012 is configured to collect data through interacting with the user. The data includes basic information of the user, for example, information like an age, a gender, a height, and a weight of the user, and the second data like drug use data and emotion data.

A feature extraction module 902 is configured to preprocess the first data (for example, a PPG signal), analyze whether the first data is missing, determine quality of the first data, extract a diabetes-related feature from the first data, and the like.

A detection module 903 is configured to perform, by the user, diabetes risk detection based on the first data and the second data, to obtain a detection result.

Optionally, the detection module 903 may further specifically include a short-term detecting module and a long-term detecting module.

The short-term detection module is configured to quickly provide the diabetes detection result by analyzing data collected in a short time, to relieve anxiety of the user in a waiting process, and reflect a short-term health status of the user.

The long-term detection module is configured to analyze data collected for a long time to provide a more accurate diabetes detection result after data is accumulated for a period of time.

An output module 904 is configured to output the diabetes risk detection result.

Optionally, if short-term detection and long-term detection are included, a short-term detection result and a long-term detection result are output.

Optionally, the system provided in this embodiment of this application further includes a health intervention module (not shown in the figure), configured to draw a diabetes risk curve based on the detection result and improvement of a plurality of monitoring results, and provide a health intervention suggestion to reflect a health status of the user.

All modules in the foregoing system may be located in a same electronic device, for example, a mobile phone or a wearable device. Optionally, the modules in the foregoing system are located in a plurality of different devices. For example, the data collection module and the feature extraction module are located in a device like a watch/band including a PPG detection module. The detection module, the output module, and the health intervention module are located in the mobile phone. For another example, there are a plurality of data collection modules, and the data collection modules may be separately located in different devices. For example, the data collection modules may be separately located in the wearable device and the mobile phone, and may collect different data.

Figure 10:
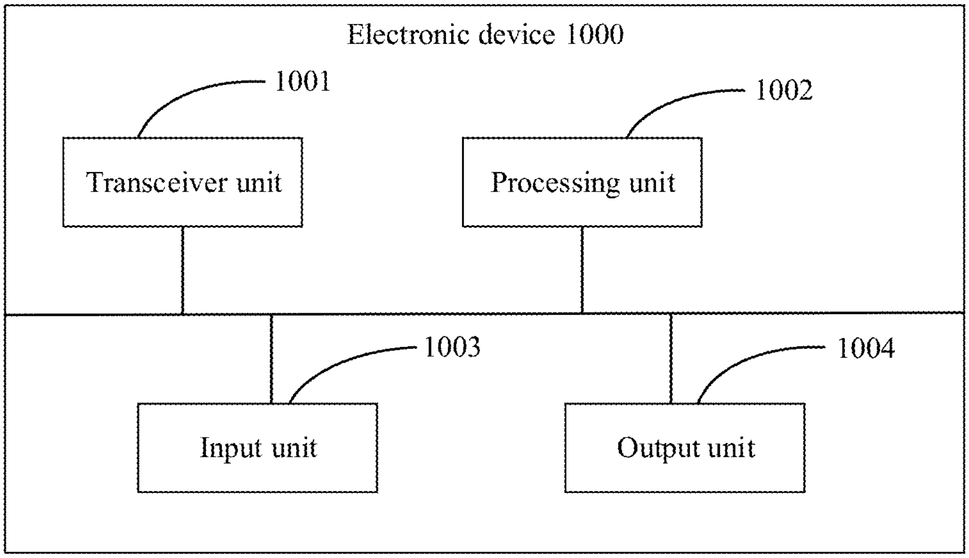
FIG. 10 is a diagram of a structure of an electronic device according to an embodiment of this application.

The following describes in detail a diabetes risk detection apparatus provided in an embodiment of this application with reference to FIG. 10.

In a possible design, FIG. 10 is a diagram of a structure of an electronic device according to an embodiment of this application. As shown in FIG. 10, the electronic device 1000 includes a transceiver unit 1001 and a processing unit 1002. As a diabetes risk detection apparatus, the electronic device 1000 may be configured to implement functions of the electronic device (the mobile phone in the foregoing embodiments is used as an example) in the foregoing method embodiments.

The transceiver unit 1001 is configured to support the electronic device in interacting with another electronic device, for example, receiving first data and/or second data from the another electronic device (for example, the wearable device in the foregoing embodiments).

The processing unit 1002 is configured to support the electronic device in performing the following step: determining a diabetes risk detection result based on the first data and the second data.

Optionally, the electronic device further includes an input unit 1003 and an output unit 1004. The input unit 1003 is configured to support the electronic device in obtaining the second data.

The output unit 1004 is configured to support the electronic device in performing the following steps: outputting the diabetes risk detection result, outputting confidence of the diabetes risk detection result, prompting a user with the confidence of the diabetes risk detection result, and the second data corresponding to the confidence, and prompting the user to edit the obtained second data or enter more second data when the confidence is less than a preset threshold.

The transceiver unit may include a receiving unit and a sending unit, may be implemented by a transceiver or a transceiver-related circuit component, and may be a transceiver or a transceiver module. Operations and/or functions of the units in the first electronic device 1000 are separately used to implement corresponding procedures of the diabetes risk detection method in the foregoing method embodiments. All related content of the steps in the foregoing method embodiments may be cited in function descriptions of corresponding functional units. For brevity, details are not described herein again.

Optionally, the electronic device 1000 shown in FIG. 10 may further include a storage unit (not shown in FIG. 10), and the storage unit stores a program or instructions. When the transceiver unit 1001 and the processing unit 1002 execute the program or the instructions, the electronic device 1000 shown in FIG. 10 is enabled to perform the diabetes risk detection method in the foregoing method embodiments.

For technical effect of the electronic device 1000 shown in FIG. 10, refer to the technical effect of the diabetes risk detection method in the foregoing method embodiments. Details are not described herein again.

In addition to a form of the electronic device 1000, the technical solutions provided in this application may also be a functional unit or a chip in the electronic device, or an apparatus that matches the electronic device.

An embodiment of this application further provides a chip system. The chip system includes a processor, the processor is coupled to a memory, and the memory is configured to store a program or instructions. When the program or the instructions is/are executed by the processor, the chip system is enabled to implement the method according to any one of the foregoing method embodiments.

Optionally, there may be one or more processors in the chip system. The processor may be implemented by using hardware, or may be implemented by using software. When the processor is implemented by using the hardware, the processor may be a logic circuit, an integrated circuit, or the like. When the processor is implemented by using the software, the processor may be a general-purpose processor, and is implemented by reading software code stored in the memory.

Optionally, there may also be one or more memories in the chip system. The memory may be integrated with the processor, or may be disposed separately from the processor. This is not limited in embodiments of this application. For example, the memory may be a non-transitory processor, for example, a read-only memory ROM. The memory and the processor may be integrated into a same chip, or may be separately disposed on different chips. A type of the memory and a manner of disposing the memory and the processor are not specifically limited in embodiments of this application.

For example, the chip system may be a field programmable gate array (FPGA), an application-specific integrated circuit (ASIC), a system on a chip (SoC), a central processing unit (CPU), a network processor (NP), a digital signal processor (DSP), a microcontroller unit (MCU), a programmable logic device (PLD), or another integrated chip.

It should be understood that the steps in the foregoing method embodiments may be completed by using an integrated logic circuit of hardware in the processor or instructions in a form of software. The steps of the method disclosed with reference to embodiments of this application may be directly performed by a hardware processor, or may be performed through a combination of hardware in the processor and a software module.

An embodiment of this application further provides a computer-readable storage medium. The computer-readable storage medium stores a computer program. When the computer program is run on a computer, the computer is enabled to perform the foregoing related steps, to implement the diabetes risk detection method in the foregoing embodiments.

An embodiment of this application further provides a computer program product. When the computer program product runs on a computer, the computer is enabled to perform the foregoing related steps, to implement the diabetes risk detection method in the foregoing embodiments.

In addition, an embodiment of this application further provides an apparatus. The apparatus may be specifically a component or a module, and the apparatus may include one or more processors and memories that are connected to each other. The memory is configured to store a computer program. When the computer program is executed by the one or more processors, the apparatus is enabled to perform the diabetes risk detection method in the foregoing method embodiments.

The apparatus, the computer-readable storage medium, the computer program product, or the chip provided in embodiments of this application are all configured to perform the corresponding method provided above. Therefore, for beneficial effect that can be achieved, refer to beneficial effect in the corresponding method provided above, and details are not described herein again.

Methods or algorithm steps described in combination with content disclosed in embodiments of this application may be implemented by hardware, or may be implemented by a processor by executing software instructions. The software instructions may include a corresponding software module. The software module may be stored in a random access memory (RAM), a flash memory, a read-only memory (ROM), an erasable programmable read-only memory (EPROM), an electrically erasable programmable read-only memory (EEPROM), a register, a hard disk, a removable hard disk, a compact disc read-only memory (CD-ROM), or any other form of storage medium well-known in the art. For example, a storage medium is coupled to a processor, so that the processor can read information from the storage medium and write information into the storage medium. Certainly, the storage medium may be a component of the processor. The processor and the storage medium may be located in an application-specific integrated circuit (ASIC).

From the descriptions of the foregoing implementations, a person skilled in the art may understand clearly that, for convenience and brevity of description, division into the foregoing functional modules is merely used as an example for description. In actual application, the foregoing functions can be allocated to different functional modules and implemented according to a requirement, that is, an inner structure of an apparatus is divided into different functional modules to implement all or some of the functions described above. For a detailed working process of the foregoing system, apparatus, and unit, refer to a corresponding process in the foregoing method embodiments, and details are not described herein again.

In the several embodiments provided in this application, it should be understood that the disclosed method may be implemented in other manners. The apparatus embodiment described above is merely an example. For example, division into modules or units is merely logical function division, and there may be another division manner during actual implementation. For example, a plurality of units or components may be combined or integrated into another system, or some features may be ignored or not performed. In addition, the displayed or discussed mutual couplings or direct couplings or communication connections may be implemented through some interfaces. The indirect couplings or communication connections between the modules or units may be implemented in electronic, mechanical, or other forms.

In addition, functional units in embodiments of this application may be integrated into one processing unit, each of the units may exist alone physically, or two or more units are integrated into one unit. The integrated unit may be implemented in a form of hardware, or may be implemented in a form of a software functional unit.

The computer-readable storage medium includes but is not limited to any one of the following: any medium that can store program code, for example, a USB flash drive, a removable hard disk, a read-only memory (ROM), a random access memory (RAM), a magnetic disk, or an optical disc.

The foregoing descriptions are merely specific implementations of this application, but are not intended to limit the protection scope of this application. Any variation or replacement within the technical scope disclosed in this application shall fall within the protection scope of this application. Therefore, the protection scope of this application shall be subject to the protection scope of the claims.

What is claimed is:

1. An electronic device, comprising:
- a processor; and
- a memory, wherein the memory is coupled to the processor, the memory is configured to store computer-readable instructions, and when the processor executes the computer-readable instructions, the electronic device is enabled to perform operations comprising:
  - obtaining first data and second data, wherein the first data comprises a photoplethysmography (PPG) signal obtained via a PPG sensor, and the second data comprises one or more of the following: diet data, exercise data, physical symptom data, drug use data, sleep data, or emotion data;
  - determining a diabetes risk detection result based on the first data and the second data;
  - outputting the diabetes risk detection result;
  - outputting a first confidence of the diabetes risk detection result, wherein the first confidence indicates accuracy of the diabetes risk detection result; and prompting a user with the first confidence of the diabetes risk detection result and the second data corresponding to the first confidence.

2. The electronic device according to claim 1, wherein the determining the diabetes risk detection result based on the first data and the second data comprises:

determining a first risk value based on the first data; and obtaining a second risk value based on the second data and the first risk value, wherein the second risk value indicates the diabetes risk detection result.

3. The electronic device according to claim 2, wherein the obtaining the second risk value based on the second data and the first risk value comprises:

obtaining the second risk value based on the first risk value and weights corresponding to different second data.

4. The electronic device according to claim 1, wherein the first confidence is determined based on at least one or more of the following: duration of the first data, whether the first data is missing within a preset time period, or a type of the second data.

5. The electronic device according to claim 1, wherein the method further comprises:

based on the first confidence being less than a preset threshold, prompting the user to edit the second data or enter third data.

6. The electronic device according to claim 1, wherein the obtaining the second data comprises:

obtaining the second data that is within a preset time period, wherein the preset time period comprises one or more of the following time periods: a time period in which the first data is missing, a nap time period, a diet time period, or a night sleep time period.

7. The electronic device according to claim 1, wherein the second data comprises a plurality of types of second data;

wherein the obtaining the second data comprises obtaining the second data in descending order of priorities of different second data; and wherein based on the first confidence of the diabetes risk detection result being greater than or equal to a preset threshold, stopping obtaining the second data.

8. The electronic device according to claim 7, wherein the method further comprises:

based on the first confidence of the diabetes risk detection result being less than the preset threshold, continuing to obtain the second data until the first confidence of the diabetes risk detection result is greater than or equal to the preset threshold.

9. The electronic device according to claim 1, wherein the diet data comprises one or more of the following: eating time, food taste or composition, or a degree of satiety;

wherein the exercise data comprises one or more of the following: exercise time, duration, an exercise intensity, or an exercise frequency;

wherein the sleep data comprises one or more of the following: a sleep time period, sleep duration, deep sleep or not, a deep sleep time period, or deep sleep duration;

wherein the drug use data comprises one or more of the following: whether a drug is used, a drug type, or a drug use frequency; and wherein the emotion data comprises one or more of the following: a psychological stress index or an emotion index.

10. The electronic device according to claim 2, wherein the method further comprises:

outputting a second confidence of the diabetes risk detection result based on the second risk value, wherein the second confidence indicates accuracy of the diabetes risk detection result.

11. The electronic device according to claim 3, wherein the method further comprises:

outputting a third confidence of the diabetes risk detection result based on the second risk value, wherein the third confidence indicates accuracy of the diabetes risk detection result.

12. The electronic device according to claim 2, wherein the obtaining the second data comprises:

obtaining the second data that is within a preset time period, wherein the preset time period comprises one or more of the following time periods: a time period in which the first data is missing, a nap time period, a diet time period, or a night sleep time period.

13. The electronic device according to claim 3, wherein the obtaining the second data comprises:

obtaining the second data that is within a preset time period, wherein the preset time period comprises one or more of the following time periods: a time period in which the first data is missing, a nap time period, a diet time period, or a night sleep time period.

14. The electronic device according to claim 1, wherein the obtaining the second data comprises:

obtaining the second data that is within a preset time period, wherein the preset time period comprises one or more of the following time periods: a time period in which the first data is missing, a nap time period, a diet time period, or a night sleep time period.

15. The electronic device according to claim 2, wherein the second data comprises a plurality of types of second data;

wherein the obtaining the second data comprises obtaining the second data in descending order of priorities of different second data; and wherein based on a second confidence of the diabetes risk detection result based on the second risk value being greater than or equal to a preset threshold, stopping obtaining the second data, wherein the second confidence indicates accuracy of the diabetes risk detection result.

16. The electronic device according to claim 3, wherein the second data comprises a plurality of types of second data;

wherein the obtaining the second data comprises obtaining the second data in descending order of priorities of different second data; and wherein based on a third confidence of the diabetes risk detection result based on the second risk value being greater than or equal to a preset threshold, stopping obtaining the second data, wherein the third confidence indicates accuracy of the diabetes risk detection result.

17. A diabetes risk detection system, comprising:

a first electronic device; and a second electronic device;

wherein the first electronic device is configured to:

receive first data and second data, wherein the first data comprises a photoplethysmography (PPG) signal obtained via a PPG sensor, and the second data comprises one or more of the following: diet data, exercise data, physical symptom data, drug use data, sleep data, or emotion data;

determine a diabetes risk detection result based on the first data and the second data;

output the diabetes risk detection result;

output a first confidence of the diabetes risk detection result, wherein the first confidence indicates accuracy of the diabetes risk detection result; and prompt a user with the first confidence of the diabetes risk detection result and the second data corresponding to the first confidence; and wherein the second electronic device is configured to obtain the first data and the second data, and send the first data and the second data to the first electronic device.

18. The diabetes risk detection system according to claim 17, wherein the determining the diabetes risk detection result based on the first data and the second data comprises:

determining a first risk value based on the first data; and obtaining a second risk value based on the second data and the first risk value, wherein the second risk value indicates the diabetes risk detection result.

19. The diabetes risk detection system according to claim 17, wherein the first confidence is determined based on at least one or more of the following: duration of the first data, whether the first data is missing within a preset time period, or a type of the second data.

20. The diabetes risk detection system according to claim 17, wherein the first electronic device is further configured to:

based on the first confidence being less than a preset threshold, prompt the user to edit the second data or enter third data.

* * * * *